| (12) | United States Patent<br>Ciaramelletti et al. | (10) Patent No.: US 9,861,151 B2<br>(45) Date of Patent: Jan. 9, 2018 |
|---|---|---|

(54) ACTIVITY MONITORING SYSTEMS AND METHODS FOR ACCIDENT DETECTION AND RESPONSE

(71) Applicant: SaPHIBeat Technologies, Inc., Redwood City, CA (US)

(72) Inventors: Carlo Ciaramelletti, Redwood City, CA (US); Marco Cavalli, Redwood City, CA (US)

(73) Assignee: SaPHIBeat Technologies, Inc., Redwood City, CA (US)

( * ) Notice: Subject to any disclaimer, the term of this patent is extended or adjusted under 35 U.S.C. 154(b) by 0 days.

(21) Appl. No.: 14/961,820

(22) Filed: Dec. 7, 2015

(65) Prior Publication Data

US 2016/0171864 A1 Jun. 16, 2016

Related U.S. Application Data

(60) Provisional application No. 62/088,466, filed on Dec. 5, 2014.

(51) Int. Cl.
*A61B 5/00* (2006.01)
*A42B 3/04* (2006.01)
(Continued)

(52) U.S. Cl.
CPC ............ *A42B 3/046* (2013.01); *A61B 5/1116* (2013.01); *A61B 5/6801* (2013.01); *A61B 5/1117* (2013.01);
(Continued)

(58) Field of Classification Search
CPC ......... A42B 3/00; A42B 3/046; A42B 3/0433; A42B 3/067; A61B 5/68; A61B 5/6801;
(Continued)

(56) References Cited

U.S. PATENT DOCUMENTS 6,453,166 B1 * 9/2002 Ishikawa ............... H04W 16/10
455/434
9,007,217 B1 4/2015 Anvari
(Continued)

OTHER PUBLICATIONS

Written Opinion dated Feb. 27, 2017 from International Application PCT/US2016/63821, 7 pgs.
(Continued)

*Primary Examiner* — Benyam Haile
(74) *Attorney, Agent, or Firm* — Ashley Sloat; Aurora Consulting LLC

(57) ABSTRACT

Various embodiments are presented for one or more wearable electronic devices which may be mounted on or integrated into, e.g., helmets, clothing, gear, vehicles, body portions, etc. These embodiments may be used in a variety of contexts in which user injury may occur, e.g., in outdoor sports, construction environments, military exercises, etc. In some embodiments, the device is comprised of motion monitoring sensors connected to a microcontroller (some embodiments may include pressure sensors, water sensors, temperature sensors, chemical sensors, sonic sensors, electromagnetic and radiation sensors, etc.). The microcontroller may perform all or a portion of a real-time analysis of motion and/or other sensor data provided by the monitoring sensors.

22 Claims, 19 Drawing Sheets

(51) Int. Cl.
    *G08B 25/01* (2006.01)
    *G01P 3/00* (2006.01)
    *A61B 5/11* (2006.01)
    *A63B 71/10* (2006.01)
    *G01L 5/00* (2006.01)
    *G01P 15/00* (2006.01)
    *G01P 1/02* (2006.01)

(52) U.S. Cl.
    CPC .............. *A61B 5/6802* (2013.01); *A61B 5/72* (2013.01); *A63B 71/10* (2013.01); *G01L 5/0052* (2013.01); *G01P 1/023* (2013.01); *G01P 3/00* (2013.01); *G01P 15/00* (2013.01); *G08B 25/016* (2013.01)

(58) Field of Classification Search
    CPC ..... A61B 5/6802; A61B 5/681; A61B 5/6813; A61B 5/6822; A61B 5/6824; A61B 5/6828; A61B 5/6803; G01P 15/00; G01P 15/18; G01P 15/023; G01P 3/00; G08B 21/02; G08B 21/0446
    See application file for complete search history.

(56) References Cited

U.S. PATENT DOCUMENTS

| | | | |
|---|---|---|---|
| 2004/0013250 A1 | 1/2004 | Kotnur et al. | |
| 2004/0132501 A1* | 7/2004 | Jiang | H04W 52/0277 455/573 |
| 2006/0189852 A1 | 8/2006 | Greenwald et al. | |
| 2006/0270949 A1 | 11/2006 | Mathie et al. | |
| 2007/0056081 A1 | 3/2007 | Aspray | |
| 2011/0172562 A1* | 7/2011 | Sahasrabudhe | A61B 5/0476 600/587 |
| 2012/0124720 A1 | 5/2012 | Evans et al. | |
| 2012/0210498 A1 | 8/2012 | Mack | |
| 2012/0304767 A1 | 12/2012 | Howard et al. | |
| 2013/0053990 A1* | 2/2013 | Ackland | G06Q 30/02 700/91 |
| 2013/0074248 A1 | 3/2013 | Evans et al. | |
| 2013/0110415 A1 | 5/2013 | Davis et al. | |
| 2013/0332286 A1 | 12/2013 | Medelius et al. | |
| 2014/0052405 A1 | 2/2014 | Wackym | |
| 2015/0186612 A1 | 7/2015 | Gartseev et al. | |
| 2015/0208750 A1 | 7/2015 | White | |
| 2015/0269825 A1 | 9/2015 | Tran | |
| 2015/0285832 A1 | 10/2015 | Thomas et al. | |
| 2015/0379351 A1* | 12/2015 | Dibenedetto | G06K 9/00671 345/633 |
| 2016/0018278 A1 | 1/2016 | Jeter, II | |
| 2016/0171864 A1 | 6/2016 | Ciaramelletti et al. | |

OTHER PUBLICATIONS

International Search Report dated Feb. 27, 2017 from International Application PCT/US2016/63821, 2 pgs.

\* cited by examiner

ACTIVITY MONITORING SYSTEMS AND METHODS FOR ACCIDENT DETECTION AND RESPONSE

CROSS REFERENCE TO RELATED APPLICATIONS

This application claims priority to and incorporates by reference U.S. Provisional Patent Application No. 62/088,466, entitled "Activity Monitoring Systems and Methods for Accident Detection and Response," filed Dec. 5, 2014.

TECHNICAL FIELD

Various of the present embodiments relate to systems and methods for detecting adverse situations and taking appropriate action.

BACKGROUND

Sport, construction, military, and law enforcement activities and other potentially hazardous situations often bear a certain level of risk. Helmets are typically used to mitigate the risk of head injury. However, in case of an accident, it is nonetheless extremely important to be able to communicate and ask for help, particularly when the user is alone, in a remote location, and/or potentially unconscious. Indeed, a clear assessment of the situation may be required for efficient assistance and proper prioritization. As another example, athletes may be in a team, but not able to communicate with teammates, e.g., because the teammate is out of sight as a result of being left behind or gone ahead of the group. In case of group activities, circumstances may arise that cause one or more members to become disconnected from the rest of the group and in need of assistance or simply unable to reconnect.

BRIEF DESCRIPTION OF THE DRAWINGS

The techniques introduced here may be better understood by referring to the following Detailed Description in conjunction with the accompanying drawings, in which like reference numerals indicate identical or functionally similar elements.

Figure 1:
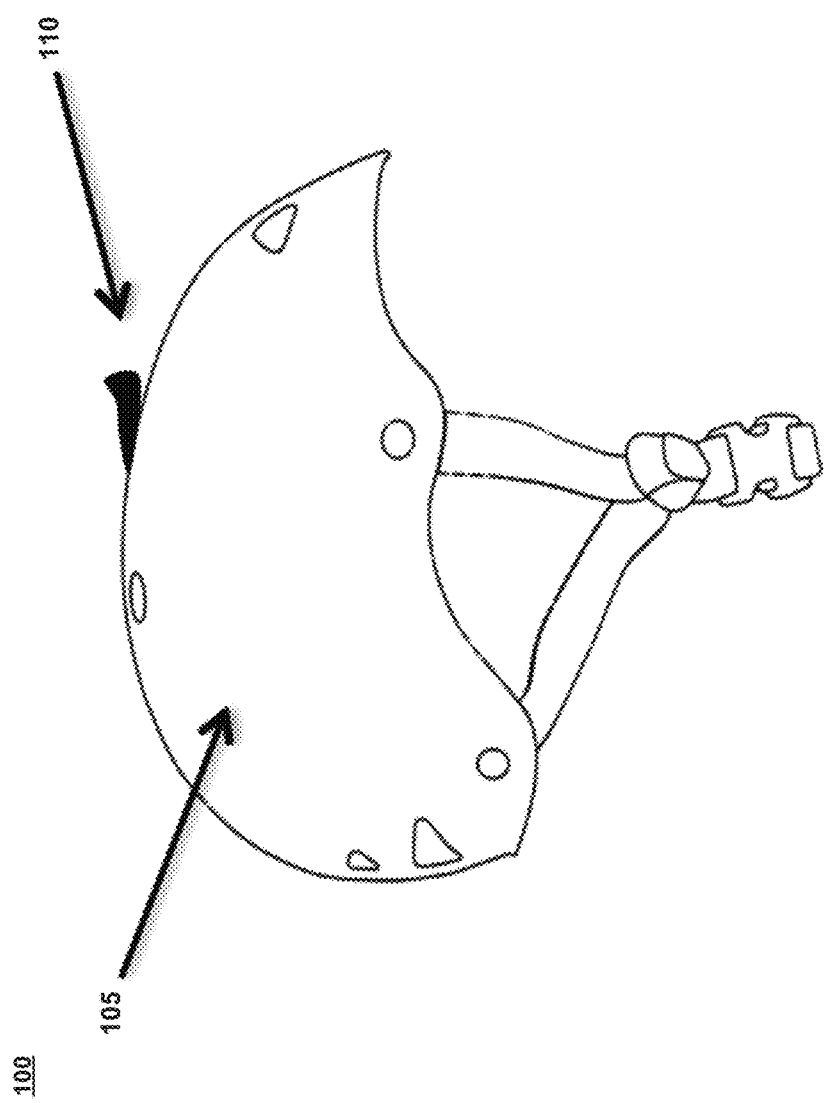
FIG. 1 is a perspective view of a helmet with an attachment as may be implemented in some embodiments.

While the flow and sequence diagrams presented herein show an organization designed to make them more comprehensible by a human reader, those skilled in the art will appreciate that actual data structures used to store this information may differ from what is shown, in that they, for example, may be organized in a different manner; may contain more or less information than shown; may be compressed and/or encrypted; etc.

The headings provided herein are for convenience only and do not necessarily affect the scope or meaning of the embodiments. Further, the drawings have not necessarily been drawn to scale. For example, the dimensions of some of the elements in the figures may be expanded or reduced to help improve the understanding of the embodiments. Similarly, some components and/or operations may be separated into different blocks or combined into a single block for the purposes of discussion of some of the embodiments. Moreover, while the various embodiments are amenable to various modifications and alternative forms, specific embodiments have been shown by way of example in the drawings and are described in detail below. The intention, however, is not to limit the particular embodiments described. On the contrary, the embodiments are intended to cover all modifications, equivalents, and alternatives falling within the scope of the disclosed embodiments.

DETAILED DESCRIPTION

Various examples of the disclosed techniques will now be described in further detail. The following description provides specific details for a thorough understanding and enabling description of these examples. One skilled in the relevant art will understand, however, that the techniques discussed herein may be practiced without many of these details. Likewise, one skilled in the relevant art will also understand that the techniques can include many other obvious features not described in detail herein. Additionally, some well-known structures or functions may not be shown or described in detail below, so as to avoid unnecessarily obscuring the relevant description.

The terminology used below is to be interpreted in its broadest reasonable manner, even though it is being used in conjunction with a detailed description of certain specific examples of the embodiments. Indeed, certain terms may even be emphasized below; however, any terminology intended to be interpreted in any restricted manner will be overtly and specifically defined as such in this section.

Overview

Various embodiments are presented for one or more wearable electronic activity monitoring devices which may be mounted on or integrated into, e.g., helmets, clothing, gear, vehicles, body portions, etc. These embodiments may be used in a variety of safety contexts in which user injury may occur, e.g., in outdoor sports, construction environments, military exercises, etc. In some embodiments, the activity monitor device is comprised of motion and position sensors connected to a microcontroller (some embodiments may include pressure sensors, water sensors, temperature sensors, chemical sensors, sonic sensors, electromagnetic and radiation sensors, etc.). The microcontroller may perform all or a portion of a real-time analysis of motion and/or other sensor data provided by the monitoring sensors (e.g., in some embodiments a remote system or a mobile phone may perform at least a portion of the analysis and response). In some embodiments the microcontroller may operate in conjunction with a remote device (e.g., a personal phone, personal digital assistant, smart watch, or smart wrist/chest bands). In some embodiments, the microcrontroller may relay the sensor data to the remote device, where the operations are performed. Based upon this analysis, the system using machine learning methods, a predictive model analysis, and a decision tree may detect an accident (physical trauma from an external source [e.g., hit by a rock, falling from a cliff, etc.], collapse due to a medical cause [e.g., exhaustion, heart attack, etc.], undesirable conditions for a given context [e.g., submersion while running, freefall while playing golf, etc.], etc.) during or following its occurrence. In particular, the system utilizes one or more models that represent the typical motion of individuals when performing certain activities (e.g., skiing, biking, running). The system continuously monitors the motion of a user using a complex motion vector to represent the user's state. When the monitored motion vector goes outside of the modeled "norm" for the activity in which the user is participating, the system triggers a secondary assessment to measure other characteristics that might reflect an accident or other medical emergency. A microcontroller that implements such a multi-stage analysis is discussed in further detail in conjunction with FIG. 11 and FIG. 12 below. As will be described in greater detail herein, one benefit of such a system is that it provides a more accurate assessment of potential emergency situations as compared to, for example, a system that relies only on the measurement of impact of a user's helmet.

In some embodiments, the system may communicate the location of the user to relevant external individuals (e.g., friends or an emergency service). In some embodiments, to guarantee reliable functionality in emergency situations, the device may implement a priority-driven power management technique based on two batteries and energy harvesting devices.

To maximize chances of a successful message delivery, in every condition, in some embodiments the device implements a multi-channel communication management algorithm based on cellphone network, satellite transmission and sub-GHz radio transmission.

The device may also be capable of collecting biometric and environmental data from other external devices or other connected sensors, combining this external data with internally collected data, and generating a detailed picture of the user's condition to improve efficiency of rescue teams. Typical data collected and transmitted may include, but not be limited to, heart rate, sweating condition, physiological stress, blood pressure, body temperature, ambient temperature, likely body position. For example, with this information the rescue team may anticipate the character of the accident, prioritize the intervention, and prepare appropriate corresponding supplies. During the "golden hour" (the initial period following an accident when first responders may be most effective in saving a victim's life or mitigating long-term health effects) such information can be especially useful and sometimes worth one or more lives.

Example System Implementation Overview

Various embodiments are directed to improving safety in potentially hazardous environments, e.g., outdoor sports. wearable/portable electronic gear mounted on or built-in into helmets.

In some embodiments, the sensor device may be placed on or integrated into helmets used in sport activities, including, but not restricted to, cycling, mountain biking, skiing, snowboarding, motorcycling, horseback riding.

FIG. 1 is a perspective view of a helmet with an attachment as may be implemented in some embodiments. A generic helmet 105 and the activity monitor device 110 mounted on it. The device case is shown in the shape of a fin, as an example, but there is no limitation or restriction on the case shape and location on the helmet. The fin may provide aerodynamic qualities facilitating its attachment to the helmet surface without interfering with the user's maneuverability.

Figure 2:
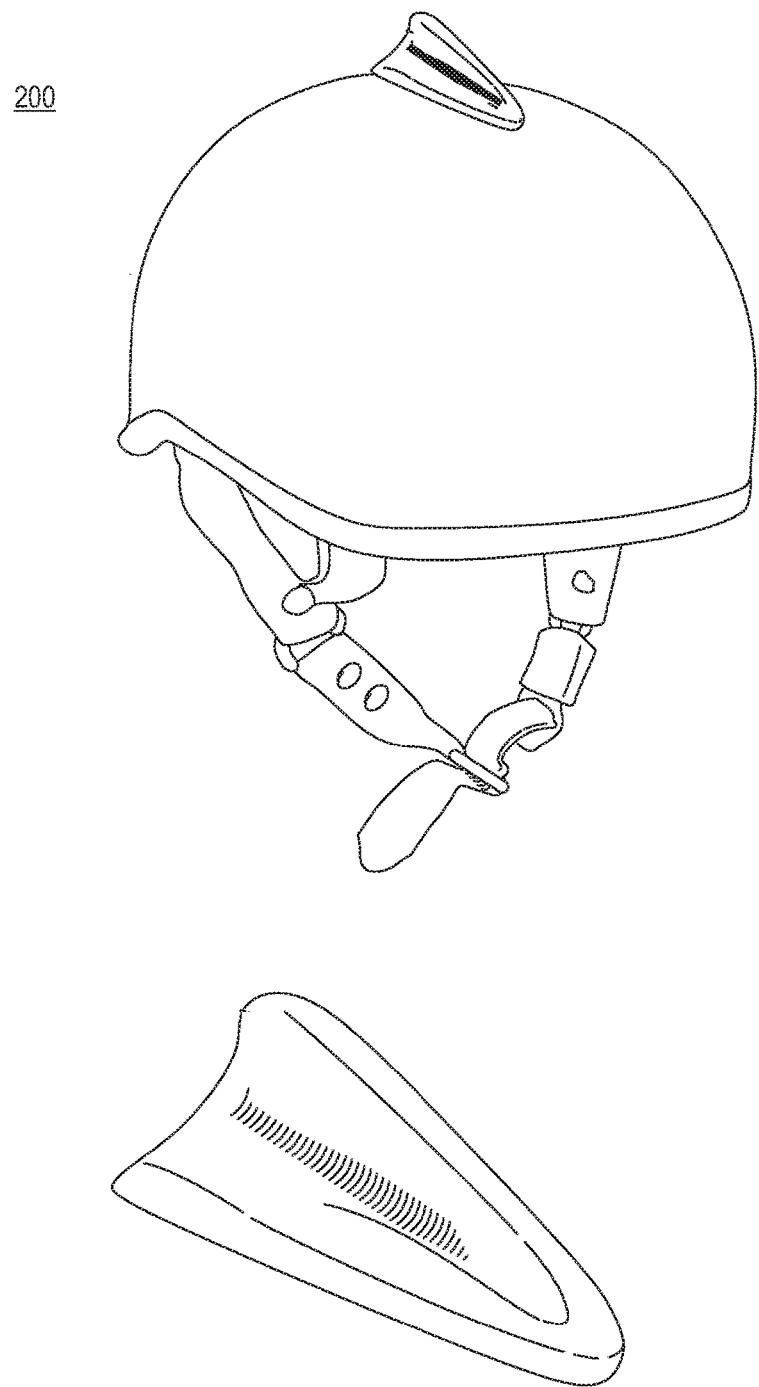
FIG. 2 is a photograph of an attachment affixed to a helmet and separate as may be implemented in some embodiments.

FIG. 2 is a photograph of an attachment affixed to a helmet and separate as may be implemented in some embodiments, though the sensor system may be integrated into the helmet or other clothing in some embodiments.

Example Sensor System

Figure 3:
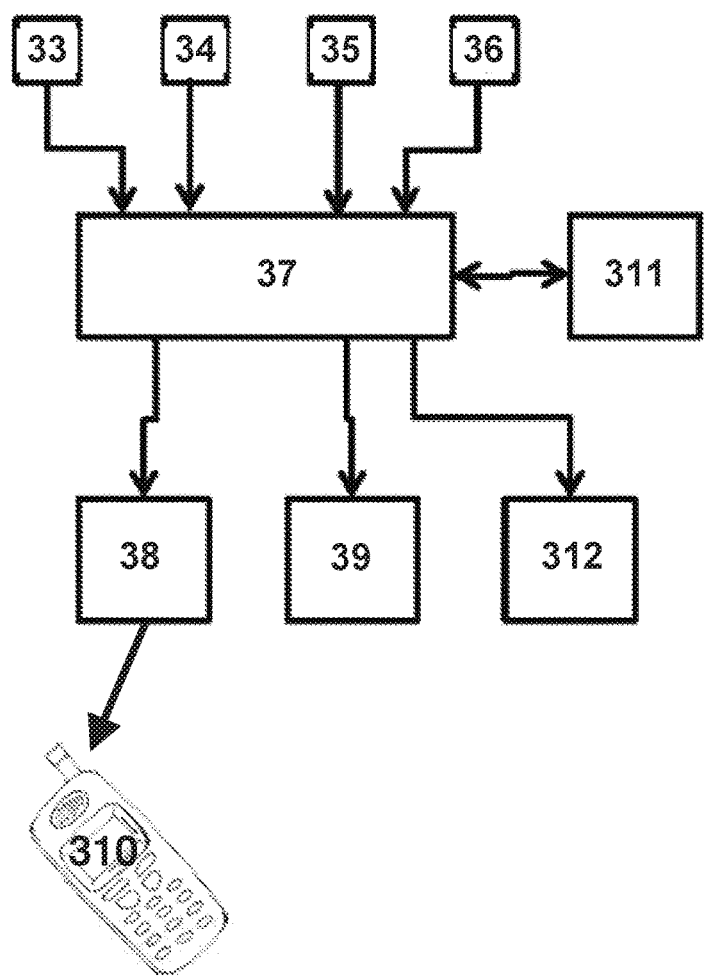
FIG. 3 is a functional block diagram of a system as may be implemented in some embodiments.

FIG. 3 is a functional block diagram of a system as may be implemented in some embodiments. Dynamic data generated by 9-axis motion sensors (3-axis accelerometer 3, 3-axis magnetometer 4, 3-axis gyroscope 35) and by an atmospheric pressure sensor 36 are supplied continuously to a microcontroller 37.

The microcontroller 37 may store the data coming from the sensors as well as processed data onto a solid-state non-volatile memory 311. The microcontroller 37 runs software that performs the following activities: a) Continuous monitoring of the motion data from the sensors; b) data analysis and comparison to the specific activity biomechanical model, looking for anomalies; c) In case of an identified anomaly, initiate a decision tree process to identify a potential accidental event; d) In case of an accident has been identified, decides the optimal strategy to communicate the user location. The activities will be discussed in further detail below in conjunction with FIGS. 13-17. Communication methods may include, e.g.: a. Via Bluetooth Low Energy 38 to a smartphone or a cellular network communication module 310; b. Via satellite transmitter 39; c. Via sub-GHz transmitter 312. Communication strategies will be discussed in further detail below in conjunction with FIG. 18. Power management by prioritizing use of battery power to privilege safety and prolong battery life in emergency conditions. Power management will be discussed in further detail below in conjunction with FIG. 12.

The accident detection algorithm may use motion data coming from sensors 33, 34, 35 and from the pressure sensor 36 to identify when the same is occurring. Some embodiments will detect any vital sign that indicate impairment for a conscious request for help in abnormal circumstances in the stated objective, as consequences of crashes, collapses, hearth attacks, excessive radiation, submersion, unexpected pressure drops, etc.

Because typical dynamics vary greatly depending on the activity and on the skill level of the user, the machine learning algorithm in some embodiments is capable of adjusting its parameters based on the two factors above to provide accurate accident recognition, minimizing errors. Factors relied upon may include, e.g., demonstrated speed, tracked figures, successful measured performances like leaning, jumping, and curve trajectories change the parameters used in the numerical dynamic model used to identify the activity anomalies. The algorithm may also use machine-learning techniques to gradually adapt over time to the dynamics typical of each user individually as the athlete's skills improve or degrade with practice or inactivity.

The solid-state non-volatile memory 311 may record the motion data for a configurable length of time. In case of an accident or other event, the memorized data can be made available to qualified rescue personnel to provide detailed information on how the events preceding and following the accident evolved.

Communication can be a key component of some embodiments. The device presented in some embodiments may be equipped with sub-GHz transmitter 312 that has an approx. 4-8 miles range of communication. In case of an accident, the device in some embodiments can automatically detect the emergency and send a distress signal, e.g., using the sub-GHz transmitter. Other similar devices in the area covered by the distress signal can automatically recognize the help request and alert the user of an emergency nearby. Through the use of the smartphone, the user who has received the distress message can locate the source of the call and provide help faster than any other entity who may be far and may have difficult access to the area.

In some embodiments, the device may work in conjunction with a smartphone application. The application may have an open interface (e.g., an open software interface), be flexible, and may be able to access other external devices that the user may be carrying and that may collect biometric data (e.g., heart rate, temperature, oxygen levels, motion, etc.). The application may combine data from the device described in this document as well as data from any other supported device, to generate a detailed portrait of the user condition in case of an accident in some embodiments. This information may be made available to qualified rescue personnel to improve rescue efficiency and immediate medical care.

Example Power Management System

Figure 4:
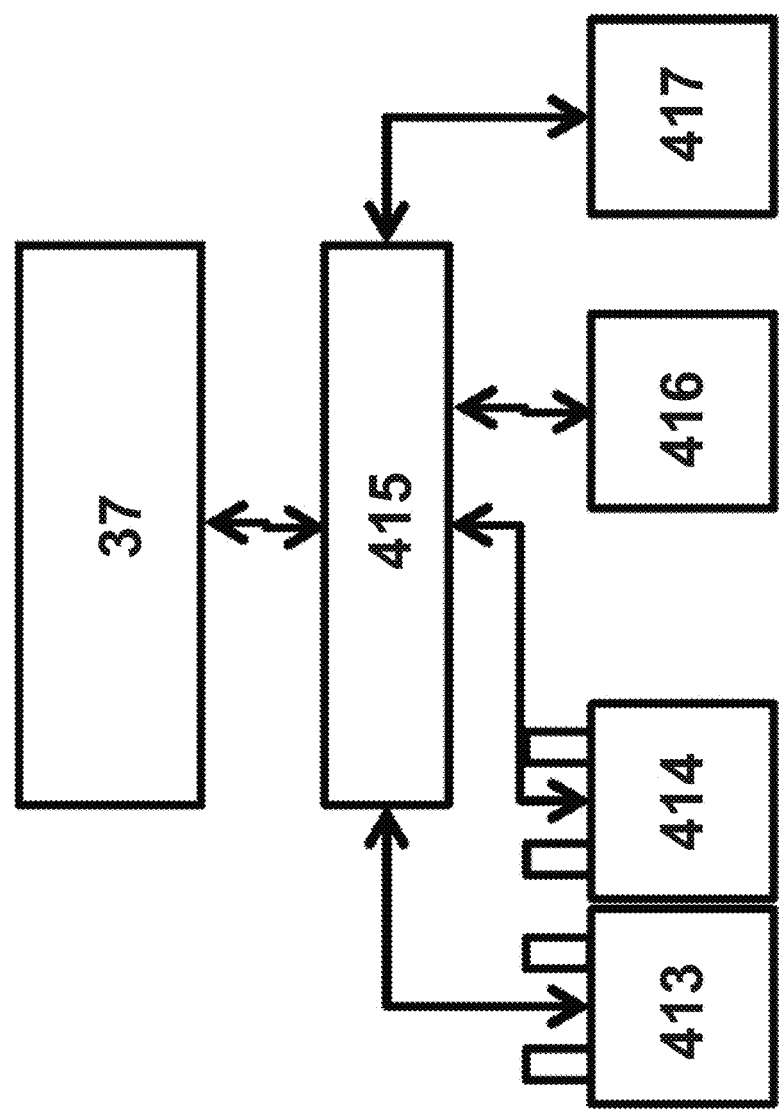
FIG. 4 is a functional block diagram of a power management system as may be implemented in some embodiments.

FIG. 4 is a functional block diagram of a power management system as may be implemented in some embodiments. In some embodiments, the device can source power from two batteries 413, 414. The microcontroller may enable one battery at a time based on a priority system. Battery 413 may be used for the normal motion monitoring operations and potentially to control other devices, such as cameras and other functionalities not critical to the safety features of the device. Battery 414 is used as an emergency use battery and comes into play only when battery 413 is depleted and in case of an emergency by deactivating any functionality not strictly needed for the management of the emergency. An algorithm running on a microcontroller may monitor the status of each battery and may decide when to switch to battery 414 and turn off redundant activities. To guarantee functionality in case of emergency the microcontroller may also enable and control additional power sources in some embodiments, e.g.: a kinetic energy harvester 416 and a photovoltaic system 417.

Example System Operation

Figure 5:
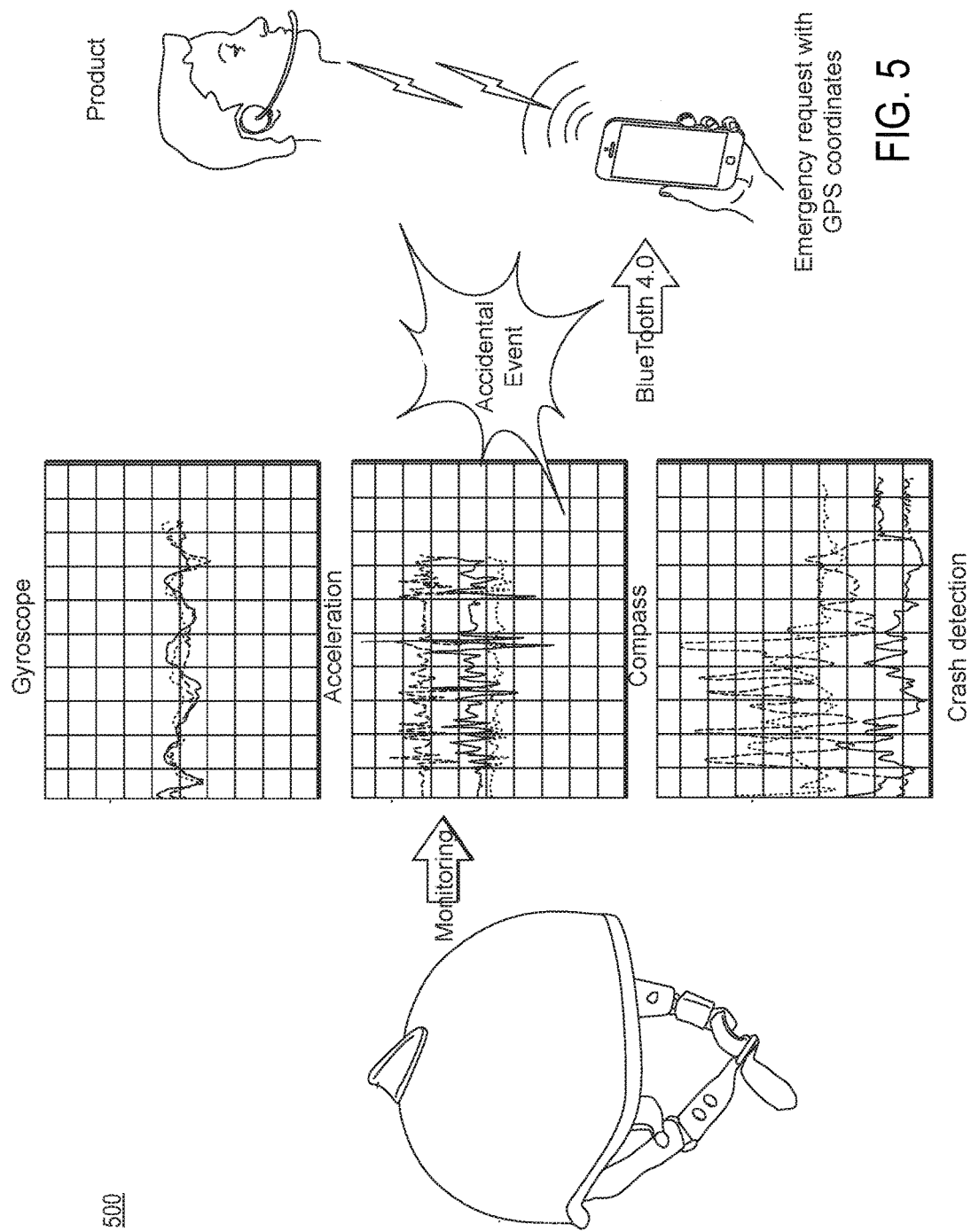
FIG. 5 is a block diagram illustrating operation of the accidental event detection system at a high level as may be implemented in some embodiments.

FIG. 5 is a block diagram illustrating operation of the detection system at a high level as may be implemented in some embodiments. As depicted, data from sensors on a head-mounted device may transmit data via, e.g., a Bluetooth connection to a mobile phone which may then contact a first responder. The mobile phone may supplement the data with, e.g., GPS coordinates and other context information.

Figure 6:
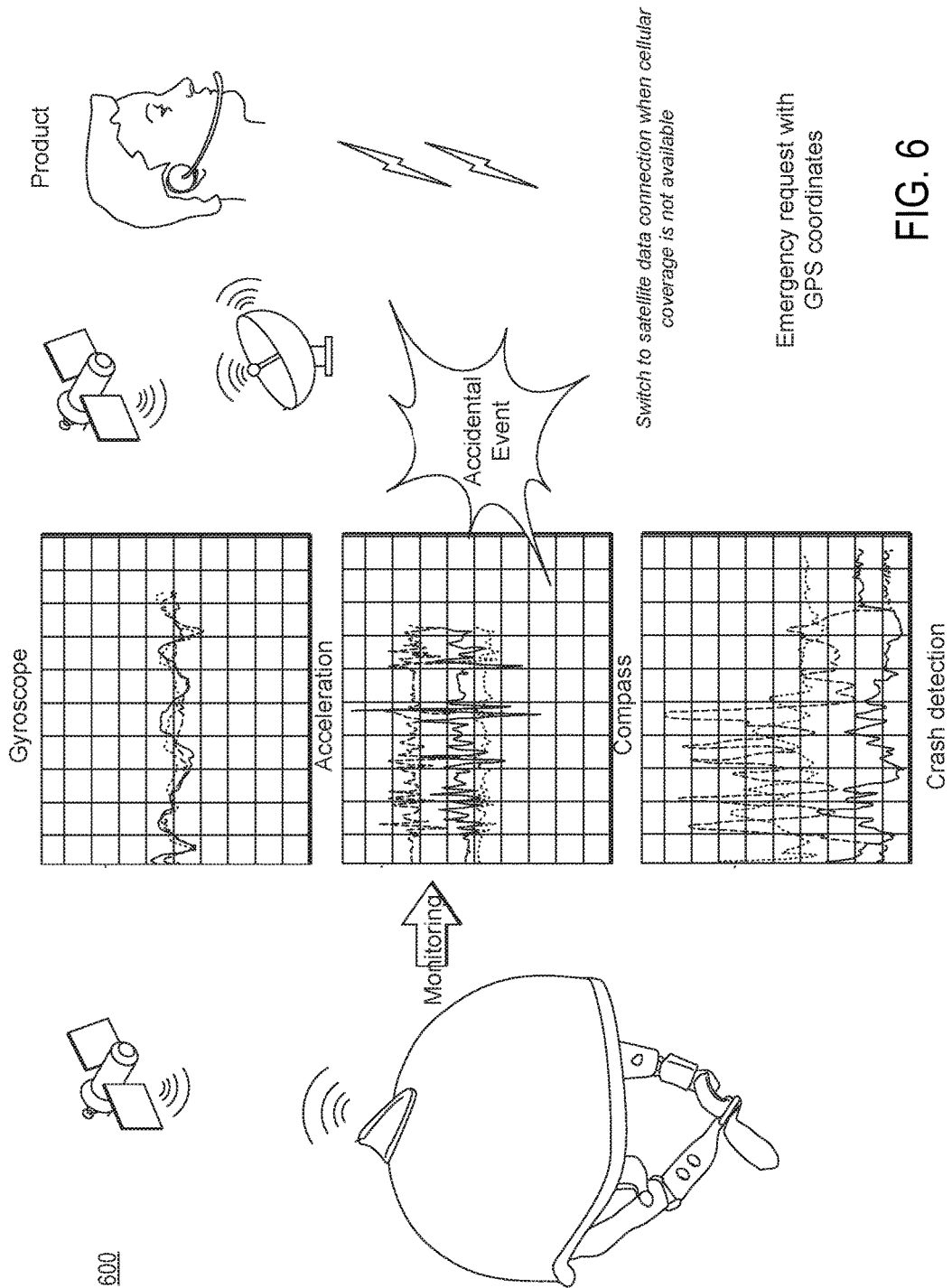
FIG. 6 is a block diagram illustrating operation of the detection system using alternative coverage at a high level as may be implemented in some embodiments.

FIG. 6 is a block diagram illustrating operation of the detection system using alternative coverage at a high level as may be implemented in some embodiments. As indicated, if cellular coverage is unavailable, the system may switch to satellite coverage. In some embodiments, the head-mounted system may include a GPS (or other position) receiver for location coordinates calculation.

Example Operational System Components

Figure 7:
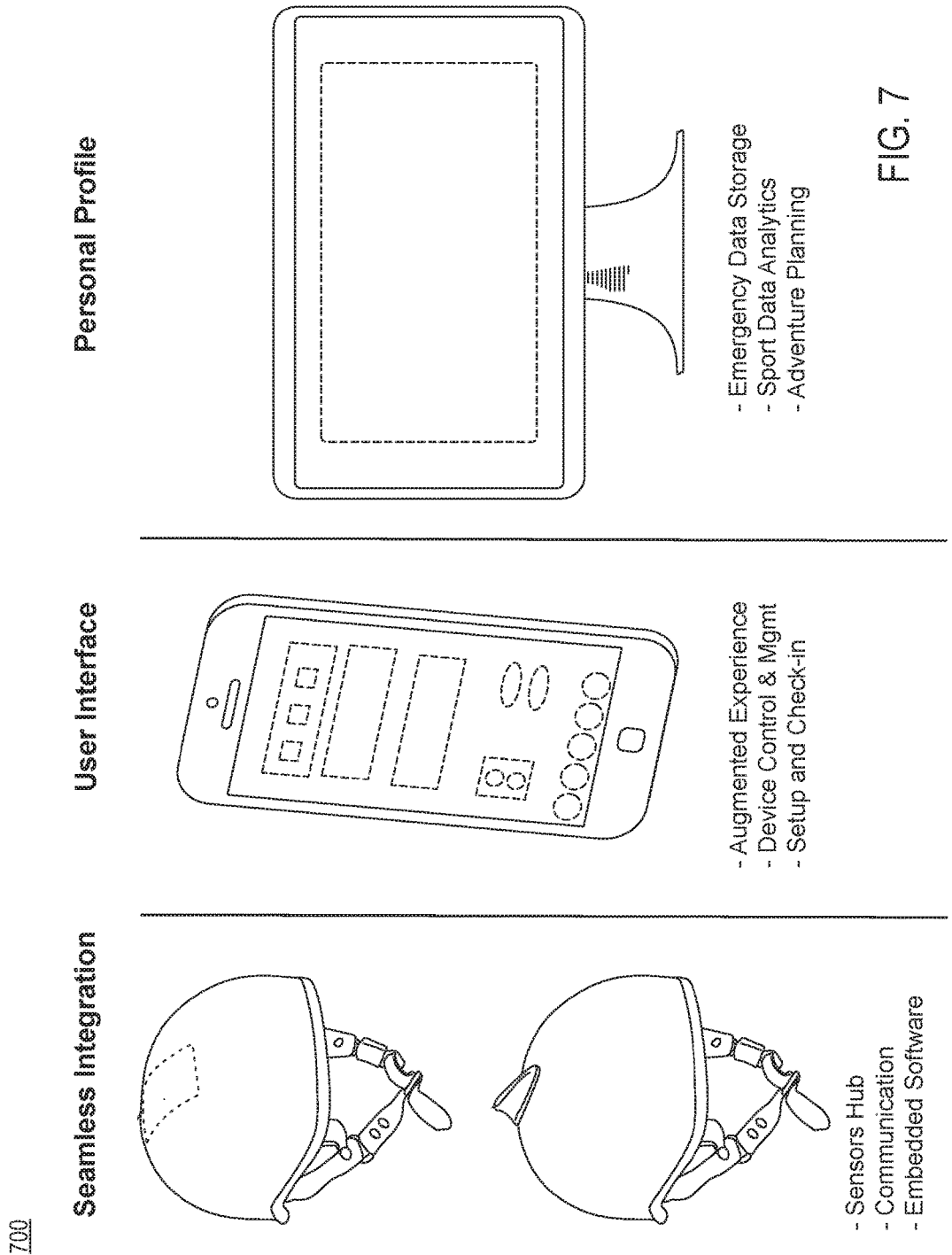
FIG. 7 is a block diagram illustrating various components in a detection and response system as may be implemented in some embodiments.

FIG. 7 is a block diagram illustrating various components in accident detection and response system as may be implemented in some embodiments.

Example Target Functionalities

Figure 8:
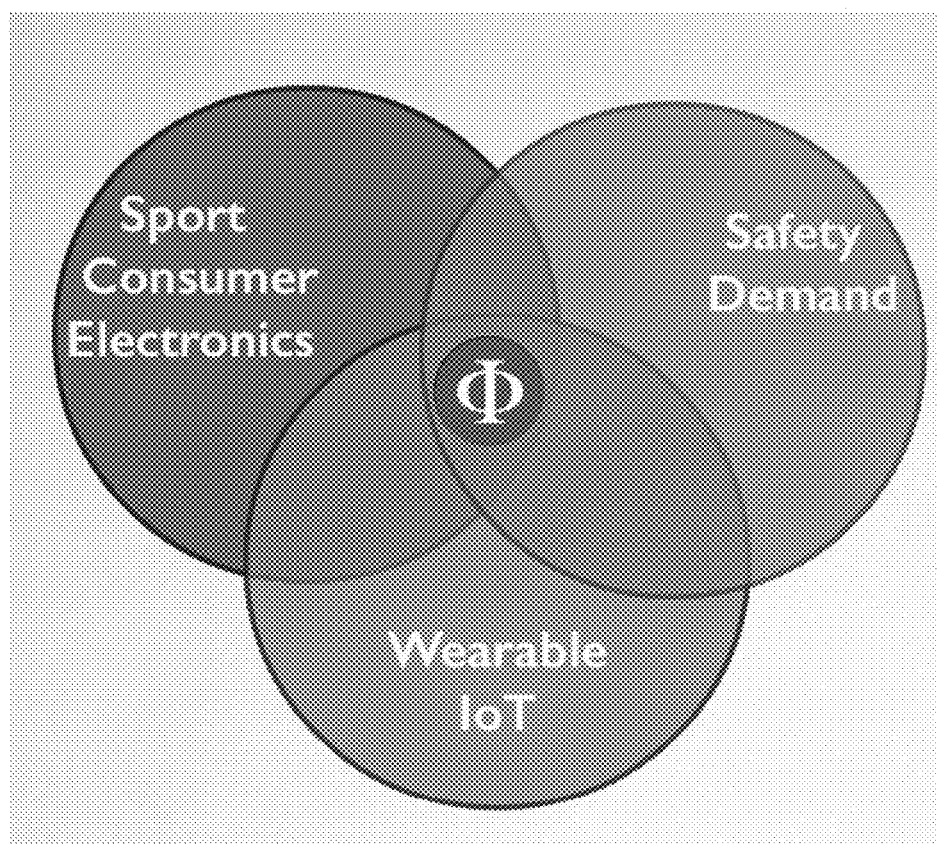
FIG. 8 is a Venn diagram illustrating various target functionalities met by certain embodiments.

FIG. 8 is a Venn diagram illustrating various target functionalities met by certain embodiments.

Example System Operation

Figure 9:
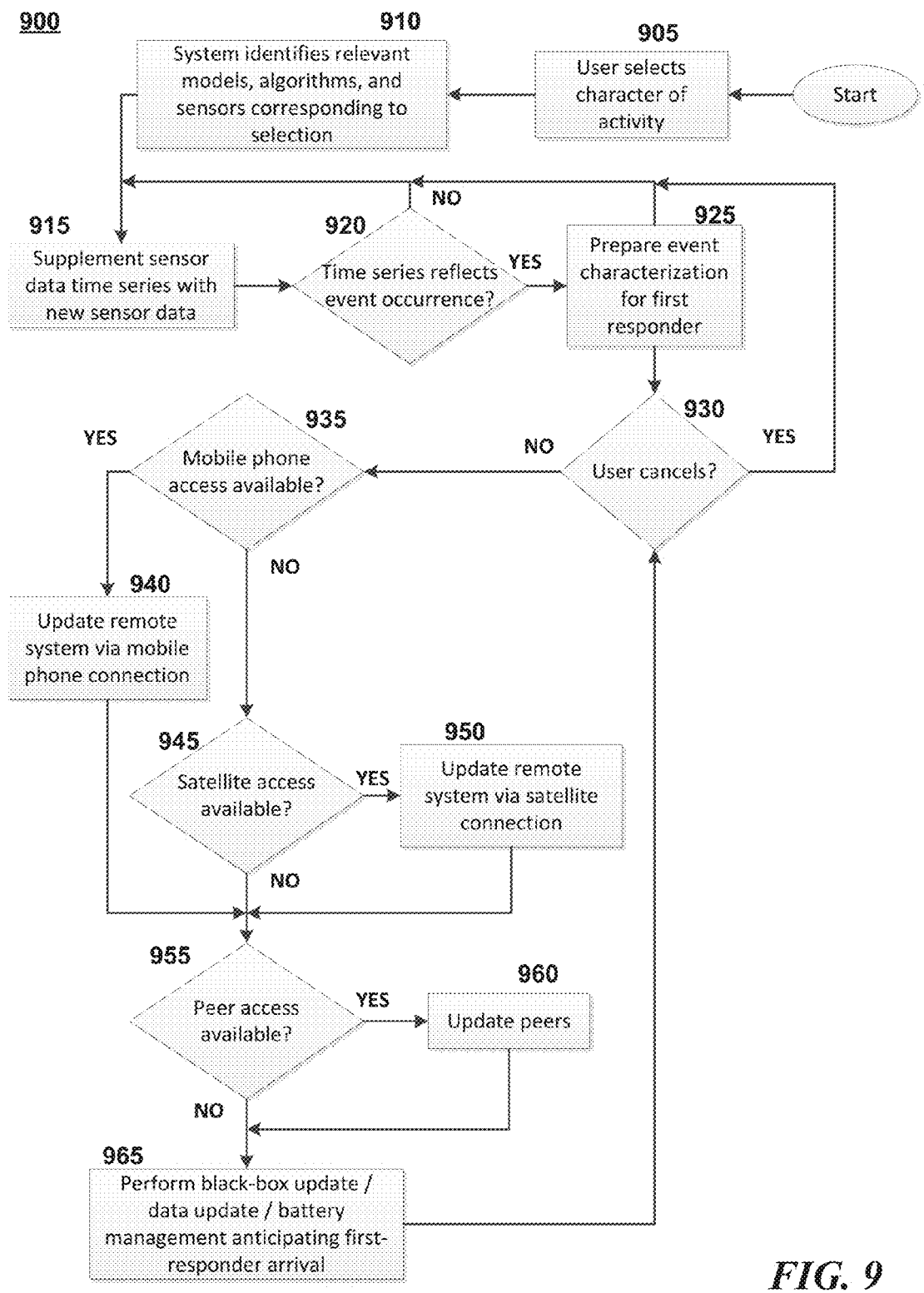
FIG. 9 is a flow diagram illustrating a process for detecting and responding to an event as may be implemented in some embodiments.

FIG. 9 is a flow diagram illustrating a process for detecting and responding to an event as may be implemented in some embodiments. At block 905, a user may select the character of the activity in which they may engage (e.g., swimming, hiking, biking, etc.). The user may make the selection via a GUI on a mobile phone, a switch on the mounted device, a Bluetooth connection etc. At block 905, the system may identify the relevant models, algorithms, and sensors for a given selection. For example, a gyroscope may be used when biking, while a temperature sensor and a submersion detection sensor may be used for water rafting.

At block 915, the system may supplement the time series of sensor data with new data. One will recognize that different sensors may update asynchronously. The system may analyze the data at block 920 to determine if an event has occurred. A frequency analysis, a Principal Component Analysis, a threshold model-based analysis, etc. may be used, alone or in combination to identify an event based on the context. If an event has been identified, at block 925 the system may prepare a characterization for the first responder. For example, for physical trauma the system may determine which body parts are most likely injured. For a drowning incident, the system may record GPS coordinates, a depth, a timestamp since the last submersion, etc. Accident identification will be discussed in further detail below in conjunction with FIG. 14-FIG. 16.

If the user has not indicated that the event was a false alarm at block 925 (e.g., the system may emit sound indicia at block 925) the system may begin a notification process. In some embodiments, the user may indicate a false alarm using a GUI on a mobile phone.

At block 935, the system may determine if it can access the mobile phone's network and if so, will communicate the event details to a remote system at block 940 (or an update to a previous submission) to precipitate a first responder response. Conversely, if satellite access is available at block 945, the system may attempt to transmit the information via satellite. If peers are available at block 955, they may likewise be notified of the event at block 960. For example, if the victim is an incapacitated biker, the system may contact the mobile phones and/or devices of other bikers in the area. Sometimes the system can use other devices as extender to bounce the request for help through the cellular phone or its satellite communication. This would be particularly useful in case the device is not capable for position or geographic location to communicate directly with the network of choice.

At black 965, the system may take actions anticipating responder arrival (e.g., manage battery power, update the event characterization with new sensor data, etc.). A black box update may be prepared so that first responders will have access to the most recent data upon arrival if the device is unable to transmit the data wirelessly. The process may continue until the user or first responder cancels the requests.

Example Feature—Sport Specific Activity Monitor, Accident Detection, and Safety Algorithm Using Dynamic Data Collected by Motion Sensor/s Integrated in or Mounted on Helmet In some embodiments, the device may be attached to or integrated into helmets used in sport activities. A sport specific accident detection and safety algorithm using dynamic data collected by motion sensor/s integrated in or mounted on helmet may be used.

Sport activities often bear a certain level of risk and accidents can happen to anyone. It is of extreme importance to be able to identify when an accident has happened, particularly if the user is practicing the sport alone or out of sight and if the user is unconscious as a result of a fall.

Some embodiments contemplate a device that includes motion sensors to monitor the user activity and motion dynamics and a microcontroller that runs an algorithm capable of analyzing the data provided by the sensors and detect an accident when that happens.

In some implementations, the device is placed on or integrated into helmets used in sport activities, including, but not restricted to, cycling, mountain biking, skiing, snowboarding, motorcycling, horseback riding.

The device may include a microcontroller, non-volatile storage memory and the following sensors: 3-axis accelerometer, 3-axis gyroscope, 3-axis magnetometer, and pressure sensor. The microcontroller may run firmware that continuously monitors the values provided by the sensors. The firmware may also include an algorithm that interprets the data provided by the sensors and is capable of recognizing when an accident is occurring.

The dynamics may greatly vary depending on the type of activity. Accordingly, the user may specify what type of activity he is engaging in and the algorithm will adjust its parameters according to one or more pre-defined models. Over time the algorithm may tune its internal parameters based on the typical motion patterns of each individual user in order to optimize accident detection capabilities and minimize the chance of false alarms.

Thus, some embodiments apply specific biomechanical models applied to the activity dynamics. A machine learning algorithm may be applied for personalized tuning of parameters. In some embodiments, predictive models for event anticipation and consistency check may be applied. In some embodiments, data analytics for safety and emergency help requests may be applied. Selectable profiles for specific activities and dynamics may be provided in some embodiments. Real time biometric monitoring for rescue intervention, prioritization and efficiency may also be provided in some embodiments.

Example Feature—Power Management Solution for Emergency/Rescue Wearable Devices

In some embodiments, the device is to be placed on or integrated into helmets used in various sport or other activities. A power management solution for emergency/rescue wearable devices may be provided in some embodiments.

Wearable devices that aim at improving safety for users may need to guarantee that they will have enough power to operate when they are needed and for the entire duration of the emergency. Thus, Power management can be a critical factor affecting reliability of such devices.

Some embodiments implement a system based upon a multiple battery mechanism and an algorithm that assigns battery resources according to specific priorities. This may ensure that at least one battery will be available in case of an emergency. Some embodiments also adopt energy harvesting techniques (e.g., kinetic and photovoltaic) to exploit motion and light to prolong battery life.

Some embodiments include a minimum of two batteries. Battery 1 may be used for the normal motion monitoring operations, potentially to control other devices, such as cameras and communication modules, and/or as a backup battery. Battery 1 may be used during an emergency in some embodiments when Battery 2 is depleted. Battery 2 may be used only in case of an emergency. An algorithm running on a microcontroller may continuously monitor the energy level of each battery and based on the amount of remaining charge may decide to disable certain non-essential functionalities to maximize battery life. Certain sensors, for example, may be temporarily disabled if not essential in a specific activity, sampling frequency may be reduced and communication minimized.

In order to extend battery life energy some embodiments employ supplemental harvesting techniques, e.g.: solar and kinetic. The algorithm may optimally manage energy harvesting devices to maximize energy storage efficiency.

Accordingly, some embodiments implement an algorithm for multi-battery management. Some embodiments employ a redundant battery architecture. Some embodiments employ multi-source energy feeding (e.g., wireless power, solar, kinetics [user motion]).

Some embodiments implement in/out gauging and reporting. Some embodiments implement self-sustainable emergency communication device with unlimited operation.

Example Feature—Multiple Sensors Architecture and Consistency Check Algorithm of Biometric Data for Unconscious 2-Way Communication and Efficient Rescue/Emergency Intervention In some embodiments, the device is to be placed on or integrated into helmets used in sport activities. In some embodiments, a multi-sensor architecture and consistency check algorithm of biometric data for unconscious 2-way communication and efficient rescue/emergency intervention are implemented.

Rescue teams may have a preference for 2-ways communication with accident victims. The rescue team may need to assess the situation and the conditions of the victim, prioritize their intervention and make sure to be equipped for best efficiency.

Sensor feedback and monitoring of the victim's conditions during the period can be vital for the successful outcome of the rescue operation. Some embodiments seek to consolidate and provide this information in the time following an accident and preceding the arrival of help. The rescue personnel can in act on the information before leaving, en route, on site, and even following retrieval.

Some people engaging in sport activities often carry multiple devices that help them monitor their performance and track their biometric data. These devices can potentially offer a wealth of information on the user health condition, but are typically used in isolation. The respective data on each device is not made available to an external or consolidated monitoring system.

Some embodiments anticipate a user carrying multiple wearable devices capable of collecting different types of data. The data from the tracking devices may be assembled it into a sophisticated model that creates an holistic picture of the user condition. The model may be open and becomes more accurate and richer the more information is made available through third party devices.

Accordingly, some embodiments contemplate using multiple sensor data collection and analysis. Some embodiments implement consistency check and reporting and provide a unique intelligent analysis and highlight system. Some embodiments implement encrypted communication and may provide mobile or web access to information through a unique key. Some embodiments provide "black box recording" for, e.g., pre- and post-accident event comparison

Example Feature—Multi-Channel Communication Strategy for Rescue Alert

In some embodiments, a multi-channel communication strategy for rescue alert may be used. For example, a rescue team may request communication with the victim following an accident. This may be difficult in remote locations and difficult geographic environments can prove extremely challenging. However, timely distress communication can be critical to maximizing the chances of survival and minimizing damage to the victim.

Some embodiments combine multiple strategies to optimize the distress communication and to maximize the rescue success rate. On a first level, when cellular coverage is available, a smartphone accompanying the victim may be used to deliver the message and/or data to first responders (communicating, e.g., via Bluetooth). If a smartphone is not available, the system may revert to satellite communication. In case particular topographical conditions prevent satellite accessibility, some embodiments use sub-GHz antennas to establish communication with similar devices that are located within a 50 miles radius of the subject. Finally, if these techniques are not available, some embodiments implement a check-in mechanism in which a server will send out an emergency alert automatically if a check-in signal from the user is not received within a predefined amount of time.

Thus, some embodiments provide a communication strategy optimized to maximize success rate based on local conditions. Some embodiments provide a power efficient strategy to maximize battery life. Some embodiments bounce a signal on neighborhood devices to bridge to the closest receiver.

Example Feature—Sub-GHz Communication Techniques for Distress Message Delivery in Case of an Accident Timely communication in case of an accident can be critical to maximize survival rate and minimize damage. Often people around the victim of an accident can provide invaluable help until professional rescue teams arrive (e.g., during the "golden hour"). These individuals represent a virtual community immediately available for first assistance. For example, other skiers can be the very first responders to an injured skier, other bikers for a knocked out biker on the curb side, companions and team mates of a climbing adventure the very first helpers, etc.

Some embodiments equip devices with sub-GHz capabilities that have an approx. 50 miles range of communication. In case of an accident, multiple users wearing the devices can automatically detect the emergency and send a distress signal, using a sub-GHz transmitter, between one another. Other devices in the area covered by the distress signal can automatically recognize the help request and alert the user of an emergency nearby. Through the use of a smartphone (if available), the user who has received the distress message can locate the source of the emergency message and provide help faster than any other entity that may be far and may have difficult access to the area.

Accordingly, some embodiments provide a peer-to-peer direct communication protocol. Some embodiments provide an in-the-range detection algorithm. Some embodiments provide multiple-variable nodes architecture and network management (e.g., as part of an ad hoc network).

Example Feature—Recording and Analysis of Motion Data for Fast and Accurate Assessment of Trauma and Optimal Rescue Intervention Often, in case of a traumatic event, rescue teams can only guess what happened and what kind of dynamics and forces the user was subject to. Hence treatment is based on best practices and a conservative approach.

By monitoring and recording the 9-axis motion of the user, some embodiments can quickly provide the rescuers with a detailed picture of how the accidental event evolved, how the user moved, what forces were applied to the user's head and what happened in the minutes following the trauma. This information can provide rescuers with an amount of objective information that can prove vital in the quick detection of critical traumas.

In some embodiments, a model can be installed on a portable device in the hands of the rescue team that can access the data from the wearable device on, e.g., the helmet. The rescuer's device may graphically reproduce the traumatic event for a quick assessment of the damage (e.g., indicating which portion of the victim's anatomy was affected).

Some embodiments implement a dynamic numerical model for the specific discipline practiced (e.g., skiing, swimming, etc.). System model may be able to precisely quantify the entity and quality of traumas.

Some embodiments implement a black-box approach for sport accidents and related injuries.

Computer System

Figure 10:
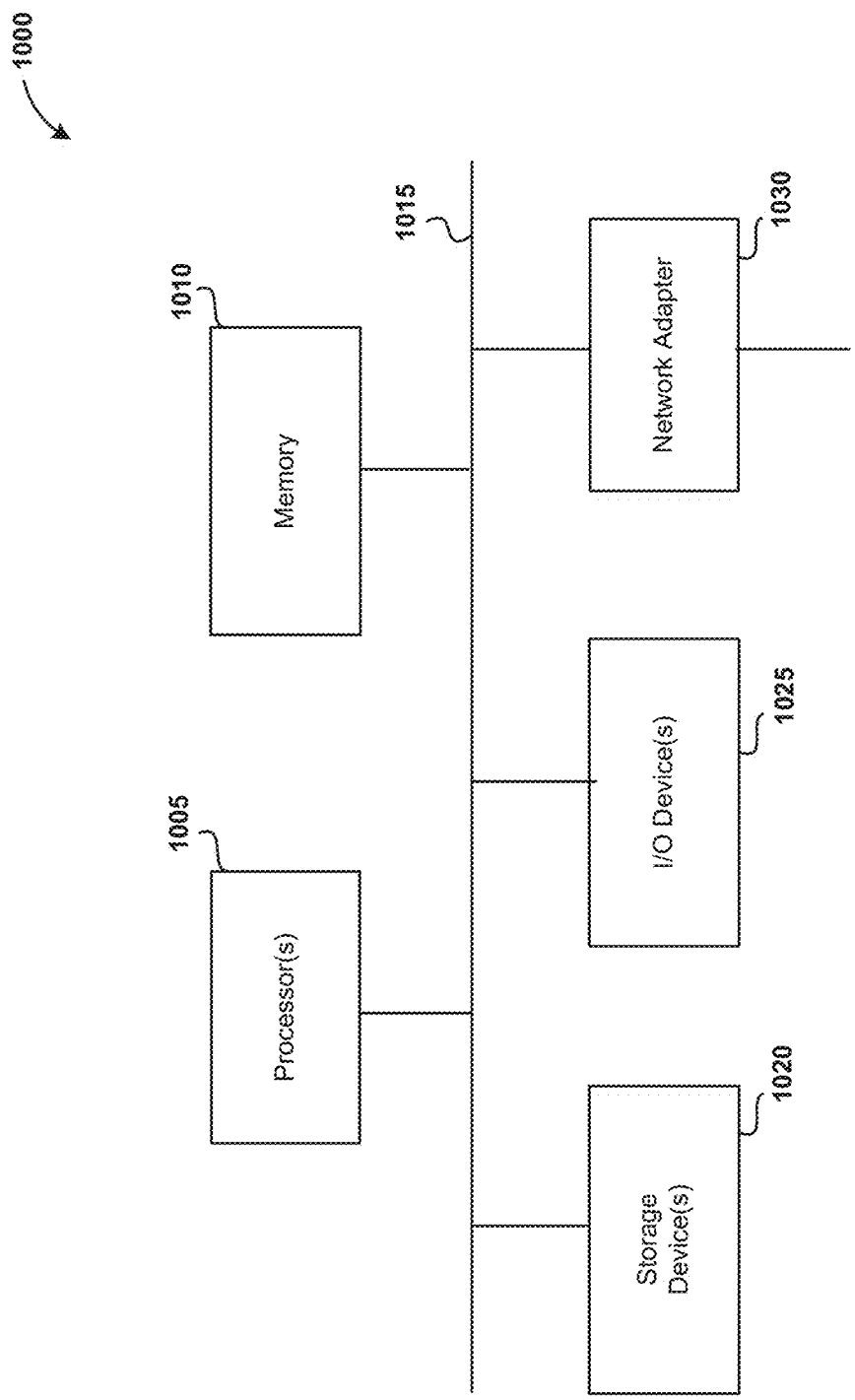
FIG. 10 is a block diagram of a computer system as may be used to implement features of some of the embodiments.

FIG. 10 is a block diagram of a computer system as may be used to implement features, e.g., navigation, object recognition, preprogrammed behavior, of some of the embodiments. The computing system 1000 may include one or more central processing units ("processors") 1005, memory 1010, input/output devices 1025 (e.g., keyboard and pointing devices, display devices), storage devices 1020 (e.g., disk drives), and network adapters 1030 (e.g., network interfaces) that are connected to an interconnect 1015. The interconnect 1015 is illustrated as an abstraction that represents any one or more separate physical buses, point to point connections, or both connected by appropriate bridges, adapters, or controllers. The interconnect 815, therefore, may include, for example, a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus, also called "Firewire".

The memory 1010 and storage devices 1020 are computer-readable storage media that may store instructions that implement at least portions of the various embodiments. In addition, the data structures and message structures may be stored or transmitted via a data transmission medium, e.g., a signal on a communications link. Various communications links may be used, e.g., the Internet, a local area network, a wide area network, or a point-to-point dial-up connection. Thus, computer readable media can include computer-readable storage media (e.g., "non transitory" media) and computer-readable transmission media.

The instructions stored in memory 1010 can be implemented as software and/or firmware to program the processor(s) 1005 to carry out actions described above. In some embodiments, such software or firmware may be initially provided to the processing system 1000 by downloading it from a remote system through the computing system 1000 (e.g., via network adapter 1030).

The various embodiments introduced herein can be implemented by, for example, programmable circuitry (e.g., one or more microprocessors) programmed with software and/or firmware, or entirely in special-purpose hardwired (non-programmable) circuitry, or in a combination of such forms. Special-purpose hardwired circuitry may be in the form of, for example, one or more ASICs, PLDs, FPGAs, etc.

Alternative Embodiments

Figure 11:
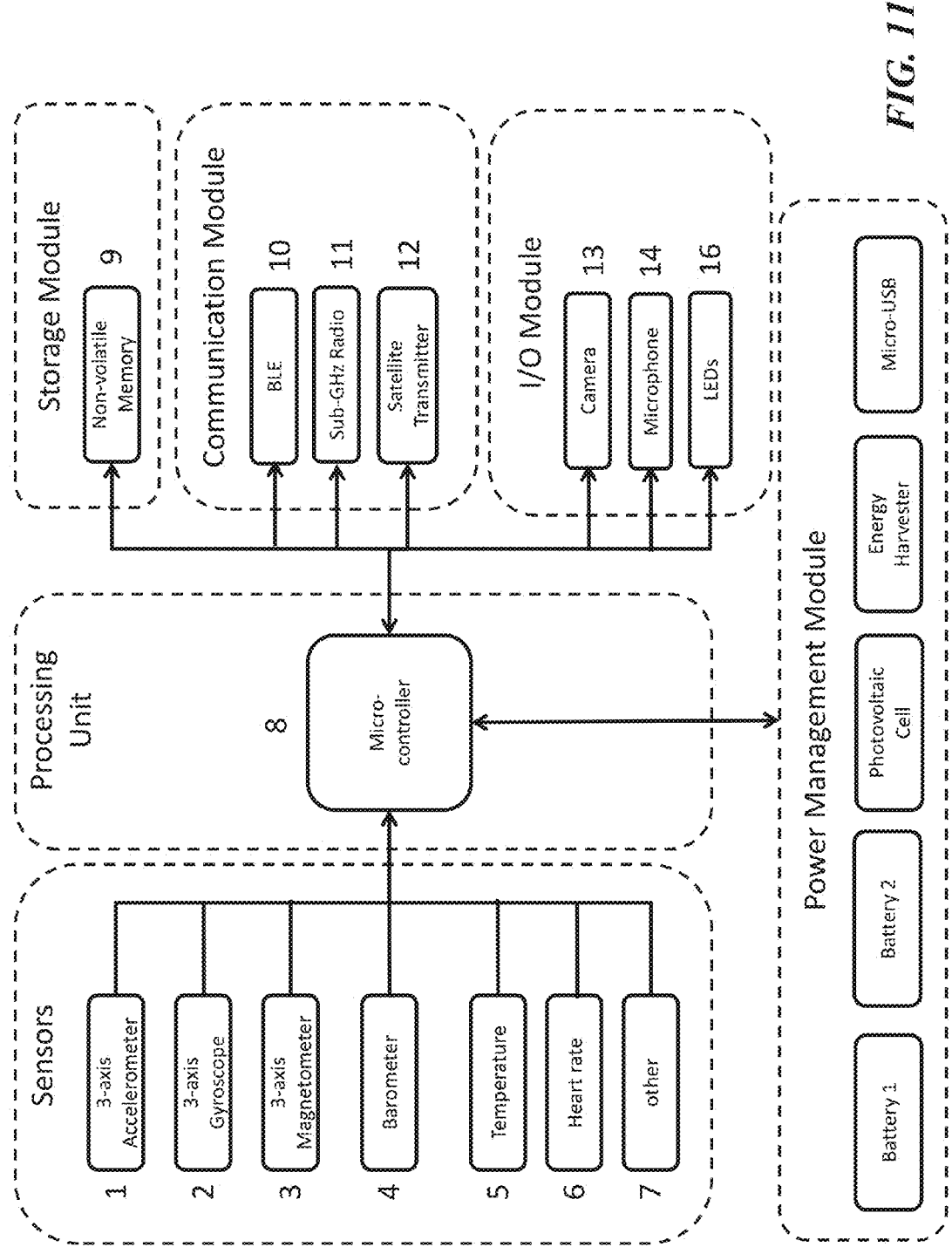
FIG. 11 is a block diagram of a system as may be implemented in some embodiments.

FIG. 11 is a block diagram of a system as may be implemented in some embodiments. Motion sensors, such as, but not limited to, a 3-axis accelerometer 1, a 3-axis gyroscope 2 and a 3-axis magnetometer 3 transmit dynamic data to a processing unit or microcontroller 8. Additional sensors may also be present in the system, including environmental sensors (e.g., a barometer 4, humidity sensor 5, or temperature sensor 5) and biometric sensors (e.g., a body temperature sensor 5, heart rate sensor 6, or other sensor 7, etc.). These additional sensors, when present, also transmit the measured data to the processing unit or microcontroller 8 for further analysis and action.

The processing unit 8 runs firmware that performs the following tasks:
Reads, at a predetermined and/or configurable sample rate, sensor data. The data may be received or read from the sensors at a specified sample rate, and the sensor values can either be analog or digital values. If necessary, sensor data may be filtered to remove the effect of noise in the sensor signals;
Stores the filtered sensor data into a non-volatile memory 9 such as, but not limited to, a flash memory or a micro SD card;
Runs an accident detection algorithm (FIG. 14) that, based on the filtered sensor data, recognizes when a potentially dangerous accident occurs to the user;
Decides the optimal communication strategy (FIG. 18) to adopt when an accident has been identified, to inform a selected list of contacts or rescue personnel of the user location and physical condition as can be inferred by sensors measurements;
Adopts the most appropriate power management strategy (FIG. 12) to ensure that enough power is available to sustain the system activity in case of an emergency;
Transmits data to an external device, such as smartphone or tablet, including raw sensor data and processed data utilizing a Bluetooth low energy (BLE) radio module 10 or any other suitable communication module, such as a sub-GHz radio module 11 and/or satellite transmitter 12 or other device; and
Manages additional input/output components, such as a camera 13, a microphone 14, and LEDs 16.

Motion, environmental, and biometric sensors 1-7 are connected to the processing unit 8, as depicted in FIG. 11. Data coming from sensors is typically affected by noise due to intrinsic sensor drift, calibration errors, and interference effects. As a result, the processing unit may adopt filtering procedures to remove undesirable noise from the sensor readings. For example, the system may apply Adaptive, Multirate, Infinite Impulse Response (IIR), and Finite Impulse Response (FIR) filters to the received sensor data. In the event that the sensors' output is analog, the processing unit performs an analog-to-digital conversion operation. To perform such conversion, the processing unit 8 may include or access an analog-digital converter (ADC).

The data stored in the non-volatile memory 9 provides a log of selected metrics concerning the activity of the user. The identity of and frequency of collection of metrics tracked by the system is configurable, and can include linear acceleration and angular velocity of the user at different time intervals. The non-volatile memory 9 may be managed as a circular buffer in which, when the total capacity is reached, the system overwrites the oldest data with new incoming data. The memory is sized, however, in a fashion to ensure that a sufficient time span of data for accident assessment is stored at all times. For example, the system may always store 30 minutes of data representing the user's most recent motion. It will be appreciated that the system may store data representing a greater or lesser amount of time, depending on memory size and frequency and amount of data being stored.

Data stored in the non-volatile memory can be transmitted to an external device (e.g., a smartphone or tablet) via the BLE module 10 or via any other available wireless or wired channel. The monitored data is used to create a model of the user activity, including information such as lean angles, trajectory, velocity, etc. of the user. The stored data can also be used, in the case of an emergency, by rescue teams, providing them with a deeper understanding of the dynamics leading to the accident and guiding emergency responders towards the adoption of the most appropriate intervention measures.

The processing unit 8 and the firmware running on it identify a potentially dangerous accident involving the user when it occurs. Accident detection is achieved by continuously monitoring data from the sensors and by using the data to create a biomechanical model of the user engaged in his/her activity. The biomechanical model represents the motion of the user while engaged in the activity. The system uses the biomechanical model to determine when the behavior of the user diverges from the expected behaviors typical of the associated activity. That is, the accident detection algorithm executed by the processing unit 8 is tailored to different activities (e.g., skiing, snowboarding, road cycling, mountain biking, etc.) because each activity is characterized by peculiar dynamics and behaviors that do not necessarily apply to others. The identification of the activity being performed can either be provided explicitly by the user or automatically detected by the system itself, through its activity recognition capabilities. Once the specific activity has been identified (either manually or automatically), the algorithm compares parameters from the biomechanical model with expected parameter values for the activity. The divergence of parameter values from the biomechanical model with the expected parameter values for the activity can suggest a potential accident. When the real time model parameters indicate that an accident may be occurring, a subsequent analysis stage is activated to closely monitor all sensor data to determine if an accident has in fact happened.

By monitoring user motion and implementing a multi-stage analysis, the system can detect not only an impact indicated by a sudden stop but other emergencies not including an impact. For example, the system would also detect if a user had a heart attack while motorcycling and slowly coasted to a stop and then passed out at the side of the road.

If the subsequent stage analysis indicates the likelihood of an accident, the system alerts the user through a visual and audible signal as well as via a message alert on an external device (e.g., a smartphone). The user is given a pre-determined amount of time to confirm that no injury has been sustained and cancel the help request. If no action is taken by the user within the pre-determined time interval, the system determines the optimal strategy to communicate a help request to a list of selected users or emergency responders. The communication strategy is based on the prioritization of the available resources. For example, if the system contains a sub-GHz radio module 11, the radio module is triggered first because it could potentially reach other users that are closest to the victim and hence in a position to provide immediate assistance. If the radio module is not present or if the communication fails using the module, the system attempts to connect to an available smartphone to determine whether there is service coverage. If service coverage exists, the smartphone is used by the system to send the help request to pre-selected contacts and/or emergency responders. If no service coverage is present or no smartphone is available (e.g., the smartphones battery is drained, the smartphone is damaged), the system attempts to use a satellite transmitter module 12 to send the help request. If the satellite transmitter 12 is available, then the system send the help request through satellite communication. If neither smartphone nor satellite transmitter is available, the system will continue to repeat a polling cycle of the communication channels at fixed time intervals, to assess whether any of the channels become available. Once a channel becomes available, the help request is sent.

The help request sent by the system may contain a variety of information that is helpful to first responders. Importantly, the help request typically includes the GPS coordinates of the user to aid first responders in locating the user. Additionally, if biometric or environmental sensor data is available, certain sensor data can also be sent as the data can be relevant to help emergency responders form a clearer picture of the accident scene and the victim's physical conditions. If a camera and/or a microphone are available, data coming from these components can be saved in the storage module and conveyed in the help request to provide additional detail that complements the overall description of the accident and the victim to rescue personnel. The help request may be a text message, an email message, a proprietary-format message, or other communication that conveys the necessary information to those who can assist the user. Alternatively or in addition to transmitting the help request, the communication module and/or I/O module can emit signals (e.g., light via LEDs 16; radio signals via BLE module 10 and/or radio module 11) to act as a beacon for emergency responders.

Figure 12:
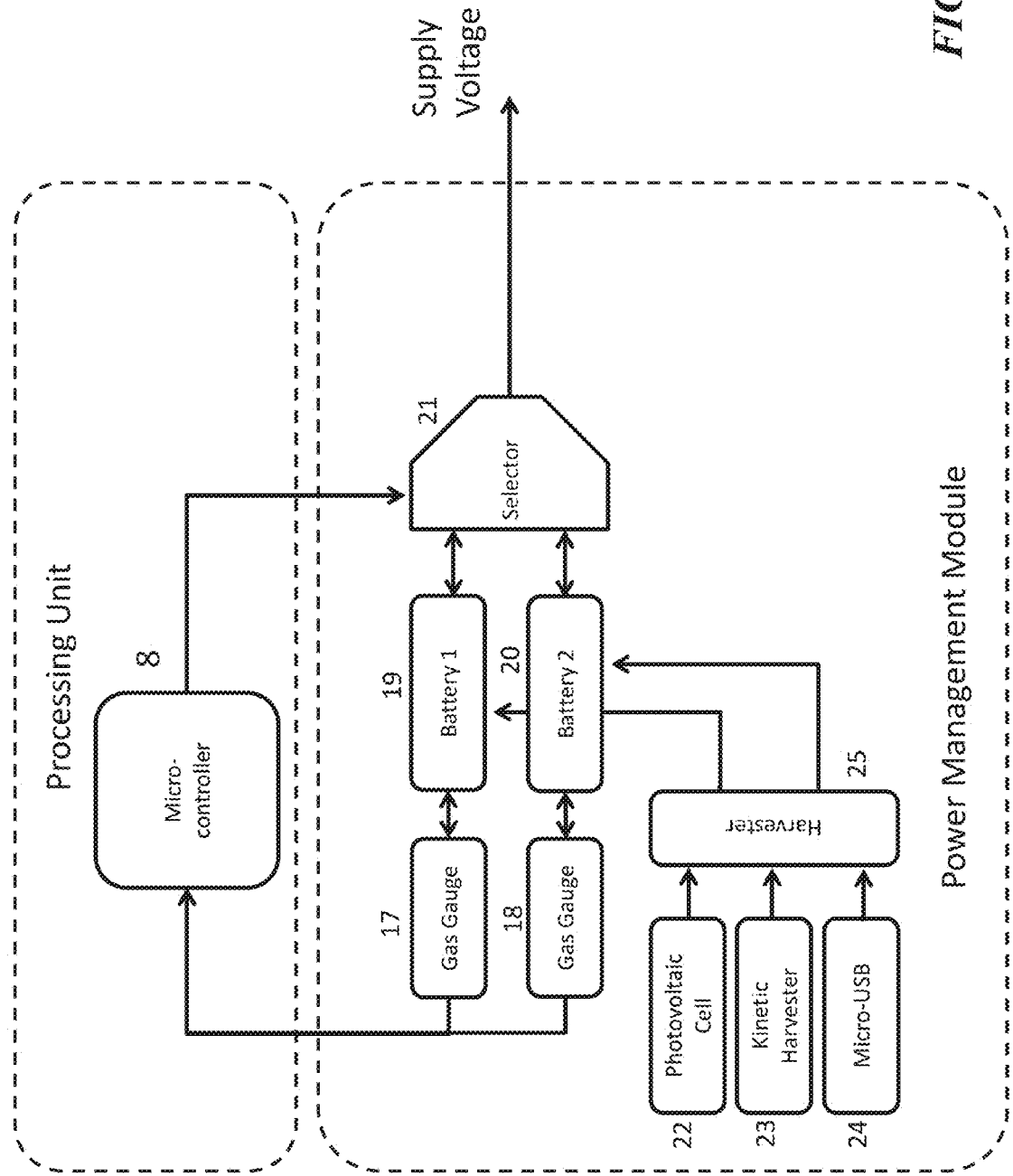
FIG. 12 is a block diagram of a power management module of the system of FIG. 11.
Figure 18:
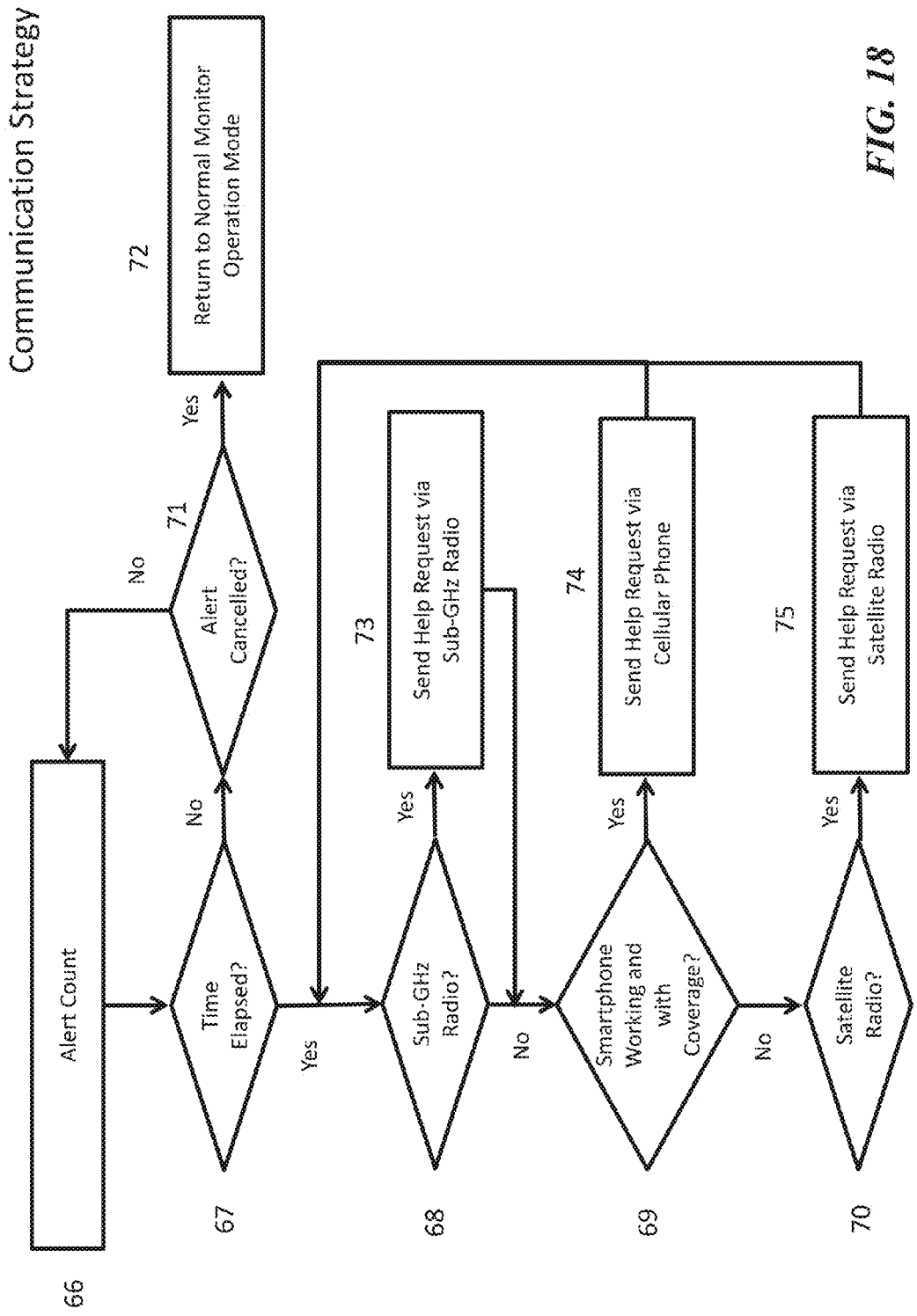
FIG. 18 is a flow diagram illustrating a process of communication strategy.

In order to ensure proper operation of the system in case of emergency, the system implements a rigorous power management policy. As shown in FIG. 12, the system uses a dual battery architecture in which one of the batteries 19 is the main power source and is used for all the regular operations (e.g., activity monitor, data transmission, communication, powering of a camera if available). A second battery 20 is a backup power source and is reserved for emergency situations. The system regularly monitors the charge level of the main battery using monitoring circuits 17, 18 and, as the charge decreases, implements power saving strategies to maximize battery life. Some non-vital functionalities may be disabled or reduced when the main battery charge level decreases beyond a pre-set threshold. If an accident has been recognized, the system may disable all non-critical functions to guarantee that enough power is available to sustain monitoring and communication capabilities until assistance is provided to the user. In such cases motion sensing features may remain operational, although at a reduced frequency of sensing, to detect activity of the victim. Communication, according to the strategy described in additional details in FIG. 18, is activated at regular time intervals to maximize the likelihood of the help request reaching the destination. To extend battery life, other power sources may be included, such as photovoltaic cells 22 and kinetic energy harvesters 23. Energy derived from light or motion may be used by a harvester 25 to recharge batteries 19 and 20. In addition, a micro USB port is provided to allow a user to directly charge batteries 19 and 20 when an external power source is available.

During normal operation the system does not communicate with external devices unless an accident is detected. At any time, however, the system can be reached and controlled by authorized external devices, such as smartphones, smartwatches or tablets, using a Bluetooth or other NFC connection. The external devices can instruct the system to transmit raw data from the sensors as well as a number of other processed information, such as quaternions or Euler's angles, that can be used by the external smart devices for advanced modeling and activity analysis. For example, the data may be accessed for subsequent performance analysis of the activity or to generate 3D visualizations of the activity that can be shared with friends and family. Through a similar mechanism the content of the non-volatile memory 9 can be transferred to other devices. For example, rescue teams can access the system and use information stored in the memory 9 as a black-box recording, providing detailed information of the dynamics before, during and after the accident.

The system, and more specifically, the processing unit 8, execute processes described in FIG. 13-FIG. 18 to identify an accident and to verify if, as a consequence of the accident, the user/wearer of the system is unable to ask for help. An automatic request for help is triggered by the system if an accident is detected and the user does not disable or otherwise prevent transmission of the help request within a certain period of time. One advantage of the disclosed accident detection process is that for an accident to be recognized it doesn't necessarily require a physical impact of the helmet or an extreme angular velocity measured outside of specific thresholds. The disclosed system is thereby able to identify accidents like, for example, falls as a result of a heart attack, heat stroke, or other accident not implying a head hit.

The accident detection algorithm implemented by the system encompasses three specific stages: (1) activity identification, (2) activity monitoring including anomalous/potential accident event identification, and (3) assessment of user condition and accident confirmation. Each stage will be described in additional detail herein.

Figure 13:
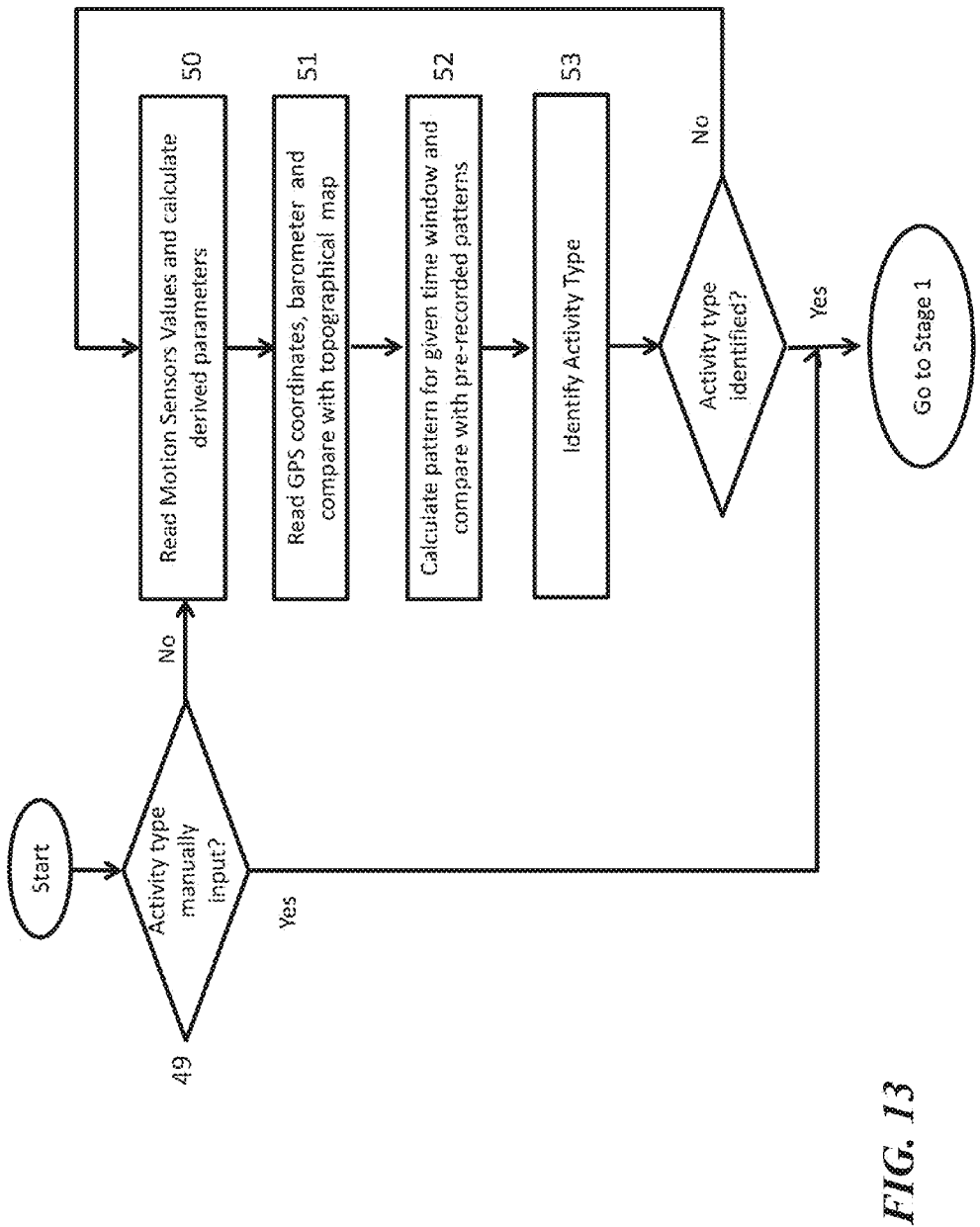
FIG. 13 is a flow diagram illustrating a process for recognizing an activity.

FIG. 13 is a flow diagram illustrating a process implemented by the system for recognizing an activity, the first stage of the accident detection algorithm. Before the beginning of an activity, at decision block 49 the user has the option to specify the type of activity he/she is going to engage in (e.g., motorcycling, road biking, skiing, etc.). A user can specify the activity through a software application running on an authorized device that communicates with the system, such as a smartphone or tablet. For example, the user may be presented with a drop down menu or radio buttons associated with potential activities, from which an activity is selected. Alternatively, the activity monitor device 105 may have physical buttons or offer other input functionality to allow the user to select the activity. The activity selection is particularly recommended for new users, until the system has the opportunity to monitor the user and derive an understanding of the typical activity profile of the user.

If the user chooses not to explicitly input the activity type at decision block 49, then the system attempts to automatically identify the activity type by analyzing a set of parameters in blocks 50-53. The parameters analyzed by the system may include, but are not limited to, location (e.g., altitude, latitude, longitude), physical constrains (e.g., on the road, off road), terrain (e.g., ski resort, park, beach, desert), speed (e.g., ski typical values, biking typical values, motorcycling typical values), acceleration patterns (e.g., gravity acceleration on a slope, motor accelerations, human propelled accelerations), trajectory patterns (e.g., curves radius, lean angle, point of sensing height), relative spatial position and movements, and biomechanical patterns (compared with historical value registered by the user). The analysis of one or more of these parameters enables the system to determine the nature of the activity that the user is performing.

The adoption of the correct activity biomechanical model is important for accurate accident identification. The activity biomechanical model is a simplified representation of the human body while performing the corresponding activity. An example of an activity biomechanical model used by the system is an Inverted Pendulum model, complemented with additional information regarding, for example, the position of the sensor (e.g., on the back of a skier or on the helmet of a biker) and user biometrics (height, weight, age). Once the activity has been recognized by the system, some key parameters and assumptions drive the creation of the biomechanical model. Some examples include the degrees of freedom of the Inverted Pendulum, the distribution of masses, typical or expected position, center of mass position, point of contacts with the ground, friction/viscosity of the ground.

At a block 50, the system reads motion sensor data (e.g., accelerometer, gyroscope, magnetometer) and calculates certain derived values (e.g., user orientation, position, linear velocity) from the motion sensor data. At a block 51, the system obtains GPS coordinates of the user either from an on-board GPS module or from a GPS module included in a connected smart device (smartphone, smartwatch, tablet, etc.). Barometer values are also read by the system. The combination of GPS and barometer readings is used by the system to obtain the accurate geographic location of the user. By locating the user on a digital topographic map it is possible to obtain information about the type of terrain surrounding the user. The surrounding terrain gives clues to the system about likely activities in which the user is engaged.

At a block 52, the system analyzes the values of the motion sensors for a pre-defined time window to extract a pattern. The pattern is compared by the system with a library of pre-determined patterns that uniquely identify each activity (e.g., skiing, motorcycling, road biking, etc.). If a pattern match is found consistent with the other analyzed data (e.g., the user location), then the activity is identified. Otherwise the system continues monitoring the user until an activity match is found. In some embodiments, the activity analysis routine runs in the background until the probability of activity identification is at least 98%. The activity recognition process enables the system to select the right activity biomechanical model for purposes of the accident detection stage.

Although not depicted in FIG. 13, the season can also be used by the system in order to assess the activity of the user. For example, the system may maintain a calendar date or may receive a calendar date from a linked mobile phone, smartwatch, or other authorized device. The season can be used in conjunction with the GPS data to select certain activities over others (e.g., hiking in the mountains in the summer months vs. skiing in the mountains in the winter months).

Figure 14:
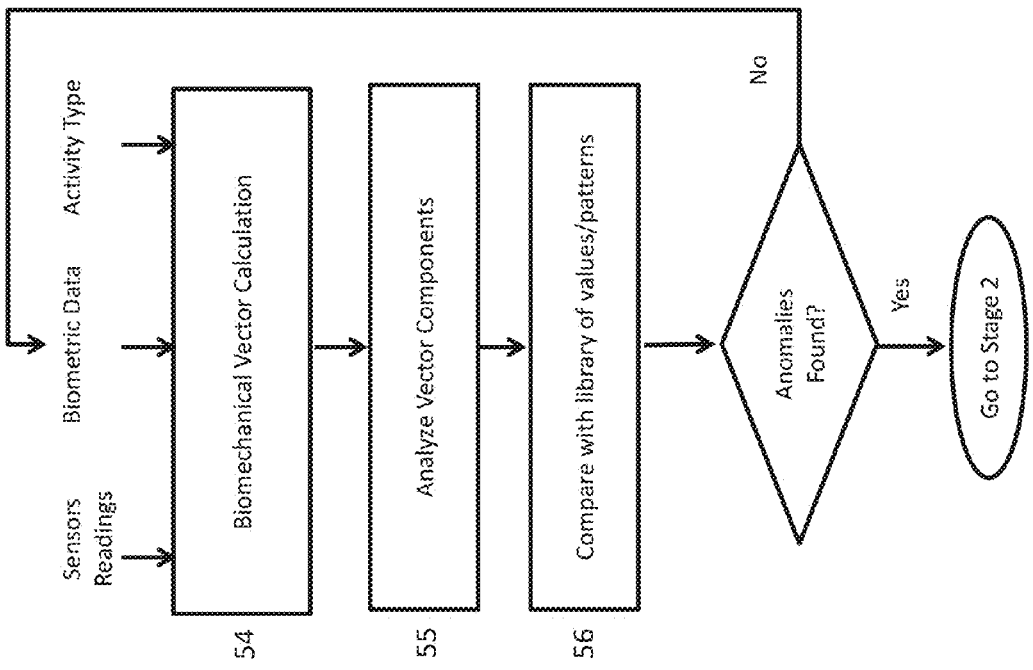
FIG. 14 is a flow diagram illustrating a process for identifying an accident.

Once the system determines the activity of the user, in the second stage of analysis the system continuously implements an accident detection process. FIG. 14 is a flow diagram illustrating a process implemented by the system for identifying an accident. Inputs to the accident detection algorithm are:

The activity type as provided by the user or assessed by the system;

Sensor readings as provided by on-board sensors; and

Optionally, biometrics data (e.g., user height, weight, age, skill-level), may be provided by the user. The user may provide the biometrics data through a graphical user interface on an authorized device (e.g., a smartphone) coupled to the system.

The system reads the sensor values and calculates certain derived values from the sensor date. The combination of both read and derived values is used by the system at block 54 to build a time-dependent, multi-dimensional biometric vector that describes the motion, the position, and orientation of the user at any given time interval. A representative biomechanical model used by the system is shown by a time-dependent matrix in FIG. 15.

Figure 15:
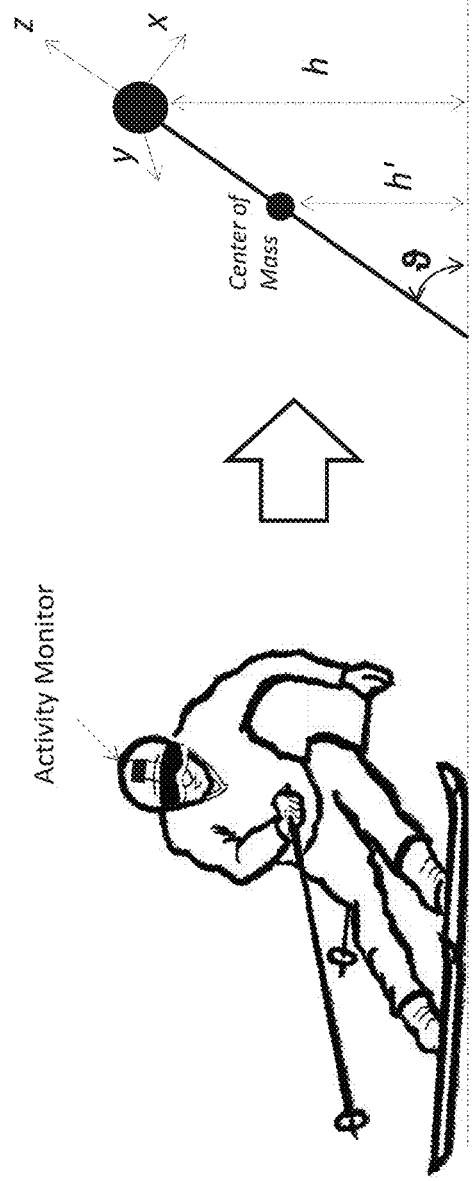
FIG. 15 shows an example biomechanical model for use in the process of FIG. 14.

In the matrix shown in FIG. 15, A is the acceleration from the accelerometer, $\bar{\omega}$ the angular velocity given by gyroscope, M the magnetic orientation from the magnetometer, Lt is the geographic latitude and Lg is the geographic longitude from the GPS, H is the altitude from the barometer, (X,Y,Z) is the relative position, V is the velocity, F is the force, $\alpha$ is the angular acceleration, and L is the angular momentum (bolded values represent vectors). Some of these values are directly measured by the sensors of the system, while others are derived by the system. Some values that the system may also take into consideration are the height, weight, center of mass, degrees of freedom, and proficiency of the athlete.

Representative formulas to calculate values for the matrix include the following:

Position $X(t)=\Sigma_{to}^{t}V(t)\Delta t$; the position location may be periodically compared to GPS geolocalization in order to improve overall accuracy Velocity $V(t)=\Sigma_{to}^{t}A(t)\Delta t$ Force $F(t)=mA(t)$ Angular Acceleration $\alpha = \frac{\Delta\bar{\omega}}{\Delta t}u$ Angular Momentum L=r m V The matrix provides instantaneous information on the user's activity and is used by the system at block 55 to build vector patterns—defined as a sequence of vectors over a period of time—that characterize the activity under analysis. The obtained sequence of vectors is stored by the system in non-volatile memory 9. Because the sensors values as well as the derived values for each time interval are stored in the non-volatile memory 9, it is possible for the system to retrieve the stored values to calculate the trajectory and the evolution over a given time interval of the user activity. Such information supports the accident detection analysis performed by the system.

The system maintains a library of values and vector patterns that characterize different activity. A pattern is a sequence of vectors over time. The library of vector patterns reflect typical or "normal" motion associated with various activities (e.g., skiing, biking, running). The library of vector patterns may also be associated with a level of mastery or activity approach (e.g., expert, intermediate, or beginner skier, or aggressive, average, or relaxed skier). For example the more the athlete is proficient with acrobatic skiing, the more patterns associated with jumps and acrobatic figures will populate the library. The library is automatically updated over time either from external input, but also from the patterns automatically generated by the system as it monitors the activity. By modifying the stored patterns that characterize each sport activity, the system is allowed to "learn" from the user's habits and become better adapted to the user's activities.

At a block 56, the system compares the monitored motion of the user with stored vector patterns that characterize "normal" parameters associated with the corresponding activity. In order to make such a comparison, the system performs one or more of the following three validity tests:

(1) The system verifies that the instantaneous values of the current user activity matrix belongs to an allowed set of values represented by a corresponding stored "normal" vector pattern associated with the user activity.

(2) The system utilizes the recent vector history (vector values at times t−1, t−2, . . . t−n) of the user and the specific activity under analysis to calculate the expected vector values for times t+1, t+2 . . . t+n. The system then verifies that the actual measured vectors for times t+1, t+2 . . . t+n fall within the predicted value ranges.

(3) The system compares the activity pattern of the user as represented by multiple stored matrices of the user's activity, with a corresponding activity pattern stored in the library. The system determines whether the pattern of activity of the user falls within allowable boundaries of the stored activity pattern, or falls outside of the boundaries of the stored activity pattern.

If one or more of the validity tests fail repeatedly for a certain period of time (from 10 to 60 seconds), the system treats such failure as a potential accident. To confirm that an accident has indeed occurred, however, the system progresses to a third stage of accident analysis.

In addition to comparing vectors and activity patterns of the user with stored vectors and patterns, it will be appreciated that the patterns (both newly generated and pre-existing) are associated with properties that represent the probability that the pattern will occur and the probability that the pattern represents a potential accident. The more the system is used, the more patterns are generated based on the user's actual behavior. Over time this makes the system more tailored to the user skills, conditions and general behavior associated with the activity under analysis. Low recurring patterns lose significance over time because they prove not to be representative of the user's typical behavior and may, at some point, be removed from the system. By removing or promoting patterns, the system adapts to the athlete proficiency, conditions, and shape. For example, at the beginning of the season a user may not be in good shape and in great form, so certain patterns may not be utilized for purposes of the comparison, but as training progresses more advanced patterns may be used by the system.

Figure 16:
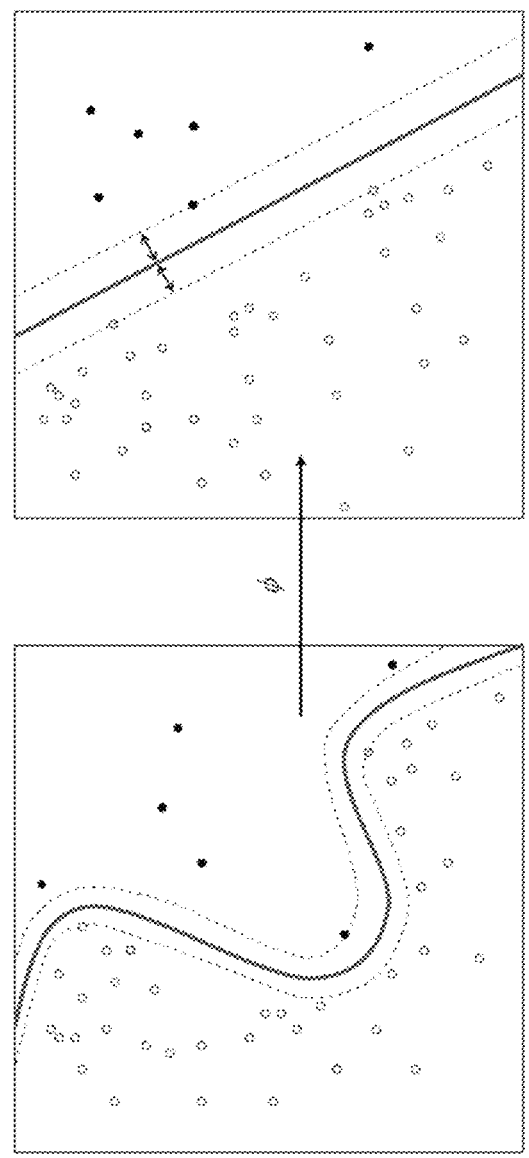
FIG. 16 is a bi-dimensional representation of system learning.

A bi-dimensional representation of how the system evolves and learns over time is illustrated in FIG. 16. Biomechanical vectors are represented by points and a solid line separates values that are "allowed" (i.e., safe, and not indicative of a potential accident) from values that are "not allowed" (e.g., may indicate a hazard condition). In FIG. 16, allowed vectors are depicted with solid points and not allowed vectors are depicted with hollow points. As the system learns more from the user's performance, the border between the regions changes, learning and adapting to the user behavior. Since the matrix is multidimensional, the same concept must be translated into a multidimensional space.

Figure 17:
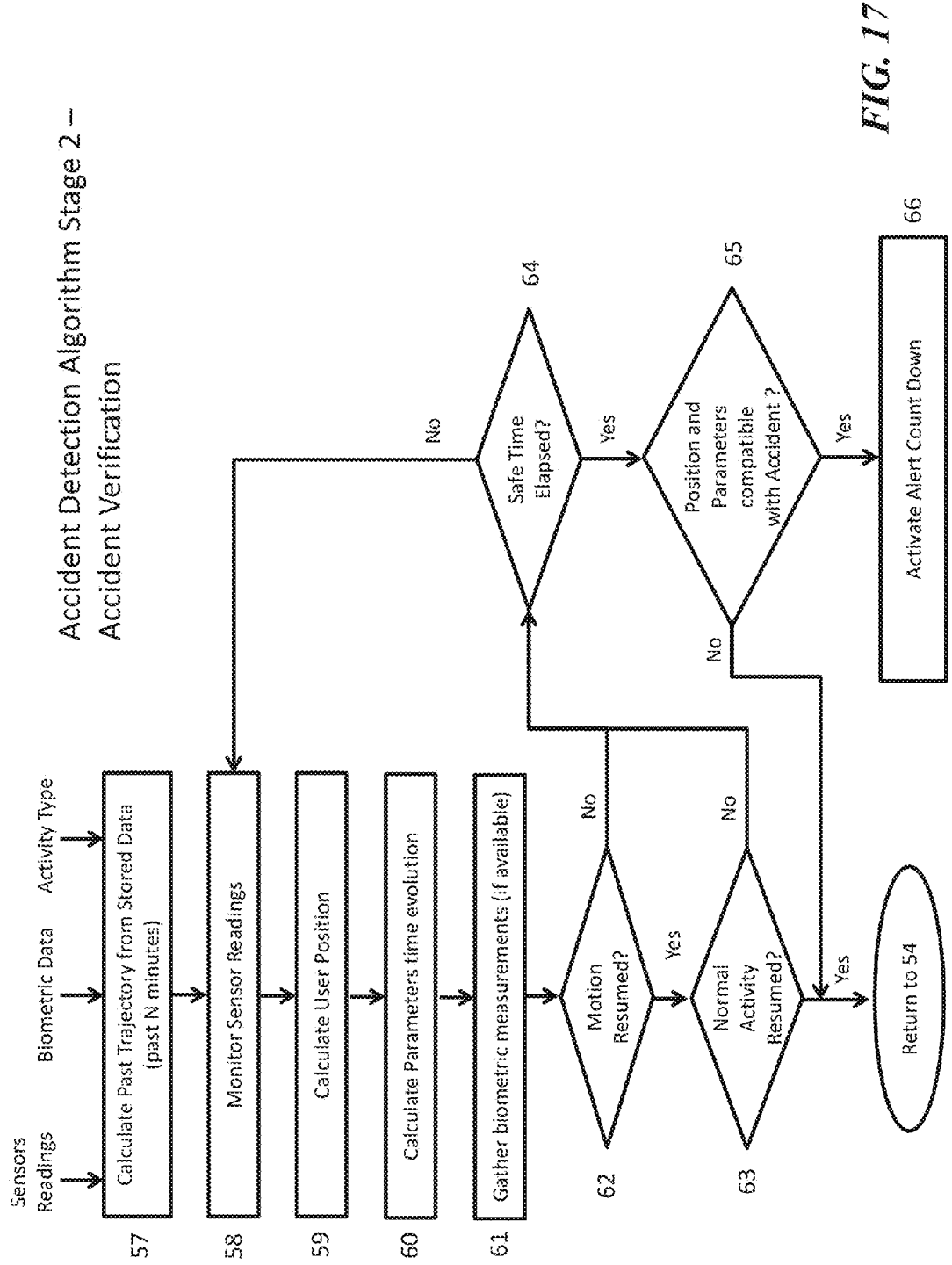
FIG. 17 is a flow diagram illustrating a process for accident verification.

FIG. 17 is a flow diagram illustrating a process that is implemented by the system to verify that an accident has occurred. As previously discussed, the system not only identifies the occurrence of an accident, but also assess whether the user is incapacitated (as a result of an accident or other reasons) and as such unable to autonomously call for help.

If the accident detection stage (FIG. 14) indicates that a potential accident has occurred, the system only knows that an anomalous event that does not match with allowed patterns has been identified. The anomalous event may or may not reflect an actual accident. A user-defined time window is therefore used to monitor activity following the detection of a potential accident, and to establish with sufficient confidence that a severe accident has occurred.

In order to confirm whether an accident requiring assistance has indeed occurred, the system implements the decision tree analysis depicted in FIG. 17 as part of a third stage of accident analysis. The sensor data provides sufficient information for the system to answer questions that reflect the state of the user, such as: Has the original activity resumed? Is the user moving or not moving? Is the movement linear or random or shaking? Is the helmet worn or not? Is the system still attached to the helmet or not? What is the user position? Orientation? Was any sharp change in the altitude measurement detected? Any abrupt change in velocity or acceleration? Was any peak force applied? Did we measure any up-side down evolution? Any flying dynamics?

Moreover, if biometric sensors (e.g., heart rate monitor, body temperatures, etc.) are available to the system, then readings from the biometric sensors may be included as part of the decision tree analysis. Anomalies in biometric readings can provide useful data on the event and on the user condition. For example, if the system has biometric data, the system can assess questions like: What's the heart rate of the user? What's the body temperature of the user?

More specifically, the system implements the following decision tree analysis. At a block 57, the system calculates the past trajectory of the user based on stored sensor data. Because all sensor values as well as the derived values for each time interval are stored in the non-volatile memory, the system can retrieve the stored values and calculate the trajectory of the user and the evolution over a given time interval of the user dynamics.

At blocks 58-59, various parameters associated with the current state of the user are assessed. At a block 58, the system continues to monitor current values from the sensors. Sensor values are continuously read and derived values are calculated to assess current activity of the user. At a block 59, the user position (e.g., standing or laying) and orientation are calculated based on sensor readings. Both the activity and position of the user may be calculated by the system at certain time intervals.

At block 60, the system assesses the evolution of certain parameter values over time windows that extend in the past (from recorded values) and continue in the present to determine whether sudden changes in values (e.g., position, acceleration, orientation) suggest that a potentially traumatic event may have occurred.

At block 61, if biometric sensors (e.g., heart rate monitor, body temperatures, etc.) are available, then readings from the biometric sensors may be gathered by the system and included as part of the decision tree analysis. Anomalies in biometric readings can provide useful data on the event and on the patient condition.

At block 62, the motion sensor readings are continuously monitored by the system to detect whether user activity resumes (after a fall, for instance) and the quality of the activity (is it a regular motion, e.g., walking or erratic movements?). At block 63, if normal motion is resumed by the user, then the event is considered non-critical (or at least the user is conscious and capable of calling for help independently) and the process returns to block 54 to continue to monitor user activity.

At block 64, if motion has not resumed or the quality of the motion is such as to suggest that the user may be severely injured, then the system continues to monitor until a pre-defined monitoring time window has elapsed. The monitored time window may range, for example, from 30-300 seconds or more. The monitored time window may vary depending on the activity of the user and the likelihood of a serious accident occurring as a result of that activity.

At a block 65, if user motion has not resumed and the pre-defined "safe" time window has elapsed, then a final analysis of the recorded parameters is assessed to confirm that an accident condition likely exists. If, for example, a sudden change in acceleration is determined, with a corresponding equally sudden change in user position and absence of movement afterwards then these—after the monitoring phase at the previous steps has completed—are considered a clear indication of a severe accident.

If the position and parameters are compatible with an accident at block 65, then processing continues to block 66. At block 66, the system activates an alert count down, with an audio and visual alert, to give the user a final chance to stop a help request from being sent. When the countdown reaches 0, the help request is sent following the communication strategy described in FIG. 18. The user is provided the ability to stop the help request within a certain, user-customizable, period of time (for example, by default 30 seconds).

If at block 66, the system instead determines that no accident occurred, the registered pattern associated with the decision tree analysis is added to the patterns library with its own recurrence value equal to 1 to indicate a low probability event. In this manner, if the user is particularly keen in acrobatic jumps and figures, motion patterns associated with those actions will be included in the library and not be considered events to be identified as potential accidents. Also if the user stops enjoying acrobatic jumps and figures, the system associates with time lower probability to happen until the pattern of such events will fade away.

FIG. 18 is a flow diagram illustrating a communication strategy implemented by the system. After the countdown timer has elapsed at block 67, if the alert is not cancelled at block 71 and the system returned to normal operation at block 72, then a help request is transmitted via sub-GHz radio (blocks 68 and 72) if available. Further, the request is also transmitted via smartphone if the smartphone has coverage (blocks 69 and 74). If not, then the request is transmitted via satellite radio (blocks 70 and 75). The process loops repeatedly to send help requests as described above.

Figure 19:
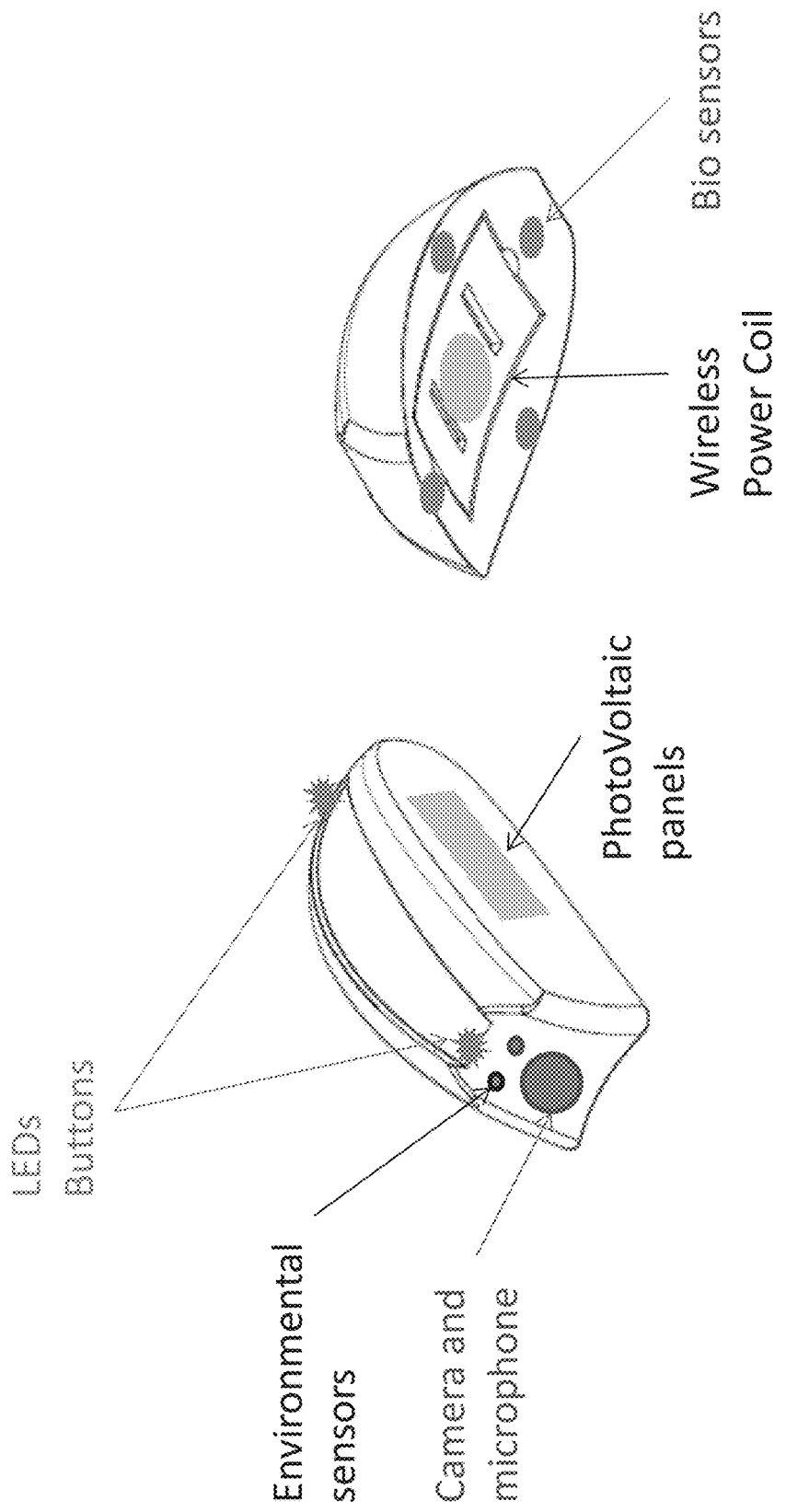
FIG. 19 is a perspective view of a system as may be implemented in some embodiments.

FIG. 19 is a perspective view of a system as may be implemented in some embodiments. The system of FIG. 19 is integrated with LEDs 16, camera 13, microphone 14, environmental sensors (e.g., temperature, pressure), photovoltaic panels 22 to generate electricity, bio sensors (e.g., heart rate, etc.) and/or wireless power coil for wireless charging. Within the system, there may also be a kinetic harvester 23. The system is a single piece with the sensors and modules etc. integrated therein. Although depicted as a stand-alone device, the system may be integrated into a helmet or other piece of gear to prevent separation of the sensors/modules etc. in the event of an accident and to help ensure that the system continues to function. For example, the system can be integrated into clothing (vest, jacket), boots, wristband, gloves, etc.

REMARKS

The above description and drawings are illustrative and are not to be construed as limiting. Numerous specific details are described to provide a thorough understanding of the disclosure. However, in certain instances, well-known details are not described in order to avoid obscuring the description. Further, various modifications may be made without deviating from the scope of the embodiments.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. One will recognize that "memory" is one form of a "storage" and that the terms may on occasion be used interchangeably.

Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any term discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given above. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions will control.

What is claimed is:

1. An emergency response system comprising:
   an activity monitoring device mounted on or integrated into a helmet, the activity monitoring device comprising:
   a plurality of sensors;
   a communication module; and
   a processor and memory coupled to the plurality of sensors and the communication module, wherein the memory has instructions stored thereon that, when executed by the processor, cause the processor to perform a method comprising:
      receiving a user input, wherein the user input comprises one or more of: a weight, a height, and an age of the user,
      acquiring a first set of sensor data with the plurality of sensors,
      identifying an activity of a user,
      combining the first set of sensor data with the user input,
      extracting an activity pattern based on the identified activity and the combined first set of sensor data with the user input, wherein the activity pattern describes one or more of: a dynamic motion of the user, an angular motion of the user, a torque exerted on the user, and a force exerted on the user while the user is performing the activity, and wherein the activity pattern comprises a sequence of vectors over time,
      comparing one or more parameters of the activity pattern against a library of allowed parameter values for the activity pattern, wherein the library further comprises a plurality of parameter values for a plurality of activity patterns related to the activity and a skill set of the user,
      detecting an anomaly if the one or more parameters of the activity pattern are outside the library of allowed parameter values, wherein the anomaly comprises an accident or a change in the skill set of the user,
      determining whether the user is incapacitated,
      identifying the anomaly as the accident when the user is determined to be incapacitated and identifying the anomaly as the change in the skill set of the user when the user is determined not to be incapacitated, and
      upon or after identifying the anomaly as the accident: transmitting a distress message indicative of an emergency to a remote system.

2. The system of claim 1, wherein the method performed by the processor further comprises transmitting the distress message only after verifying the anomaly, wherein verifying the anomaly includes: determining if the activity has resumed by: updating the activity pattern with a second set of sensor data acquired after the anomaly, and comparing the updated activity pattern to the library.

3. The system of claim 1, wherein the method performed by the processor further comprises updating the library for the identified activity based on the activity pattern when the anomaly is not indicative of the emergency.

4. The system of claim 1, wherein the identifying the activity of the user comprises determining a geographical position of the user and comparing the geographical position to a map to determine a terrain and an associated activity for the terrain.

5. The system of claim 1, wherein the identifying the activity of the user comprises comparing the first set of sensor data over time with known patterns of known activities to find a match between the first set of sensor data and the known activities.

6. The system of claim 1, wherein the one or more parameters comprise one or more of: an instantaneous value within the activity pattern, an expected vector value for the activity pattern, a sensor data value, and a derived value from the activity pattern.

7. The system of claim 1, wherein the comparing the activity pattern comprises calculating a range of expected vector values for the activity based on recent vector history and the identified activity, and verifying whether one or more measured values fall within the expected range of vector values.

8. The system of claim 1, wherein the comparing the activity pattern comprises comparing a consistency of the activity pattern with one or more allowed parameter values for the activity pattern corresponding to the identified activity.

9. The system of claim 1, wherein the method performed by the processor further comprises measuring one or more biometrics of the user, wherein the distress message further includes an indication of a biometric anomaly of the user, and wherein the one or more biometrics include: a heart rate, a body temperature, a sweating condition, a state of physiological stress, a blood pressure, or a body position.

10. The system of claim 1, wherein the method performed by the processor further comprises transmitting the distress message via one or more communication channels depending on channel availability.

11. The system of claim 1, further comprising a power management module comprising a first power source and a second power source, wherein the power management module is configured to operate primarily on the first power source and maintain the second power source in reserve for transmission of the distress message.

12. A non-transitory computer-readable medium having stored thereon instructions to cause a processor to execute a method, the method comprising:
   receiving a user input, wherein the user input comprises one or more of: a weight, a height, and an age of the user,
   acquiring a first set of sensor data using an activity monitoring device mounted on or integrated into a helmet, the activity monitoring device comprising a plurality of sensors, a communication module, memory, and the processor, wherein the plurality of sensors is communicatively coupled to the processor;
identifying an activity of a user;
combining the first set of sensor data with the user input,
extracting an activity pattern based on the identified activity and the combined first set of sensor data with the user input, wherein the activity pattern describes one or more of: a dynamic motion of the user, an angular motion of the user, a torque exerted on the user, and a force exerted on the user while the user is performing the activity, and wherein the activity pattern comprises a sequence of vectors over time;
comparing one or more parameters of the activity pattern against a library of allowed parameter values for the activity pattern, wherein the library further comprises a plurality of parameter values for a plurality of activity patterns related to the activity and a skill set of the user;
detecting an anomaly if the one or more parameters of the activity pattern are outside the library of allowed parameter values, wherein the anomaly comprises an accident or a change in the skill set of the user;
determining whether the user is incapacitated;
identifying the anomaly as the accident when the user is determined to be incapacitated and identifying the anomaly as the change in the skill set of the user when the user is determined not to be incapacitated; and
upon or after identifying the anomaly as the accident:
transmitting, using the communication module, a distress message indicative of an emergency to a remote system.

13. An emergency response method performed on or by an activity monitoring device mounted on or integrated into a helmet, the method comprising:
receiving a user input, wherein the user input comprises one or more of: a weight, a height, and an age of the user;
acquiring a first set of sensor data with a plurality of sensors communicatively coupled to the activity monitoring device;
identifying an activity of a user;
combining the first set of sensor data with the user input;
extracting an activity pattern based on the identified activity and the combined first set of sensor data with the user input, wherein the activity pattern describes one or more of: a dynamic motion of the user, an angular motion of the user, a torque exerted on the user, and a force exerted on the user while the user is performing the activity, and wherein the activity pattern comprises a sequence of vectors over time;
comparing one or more parameters of the activity pattern against a library of allowed parameter values for the activity pattern, wherein the library further comprises a plurality of parameter values for a plurality of activity patterns related to the activity and a skill set of the user;
detecting an anomaly if the one or more parameters of the activity pattern are outside the library of allowed parameter values, wherein the anomaly comprises an accident or a change in the skill set of the user;
determining whether the user is incapacitated;
identifying the anomaly as the accident when the user is determined to be incapacitated and identifying the anomaly as the change in the skill set of the user when the user is determined not to be incapacitated; and
upon or after identifying the anomaly as the accident:
transmitting a distress message indicative of an emergency to a remote system.

14. The method of claim 13, further comprising:
verifying the anomaly, wherein verifying comprises:
determining if the activity has resumed by updating the activity pattern with a second set of sensor data acquired after the anomaly, and
comparing the updated activity pattern to the library; and
transmitting the distress message only after verifying the anomaly.

15. The method of claim 13, further comprising updating the library for the identified activity based on the activity pattern when the anomaly is not indicative of the emergency.

16. The method of claim 13, wherein identifying the activity of the user comprises determining a geographical position of the user and comparing the geographical position to a map to determine a terrain and an associated activity for the terrain.

17. The method of claim 13, wherein the identifying the activity of the user comprises comparing the first set of sensor data over time with known patterns of known activities to find a match between the first set of sensor data and the known activities.

18. The method of claim 13, wherein the dynamic motion comprises one or more of: an acceleration, a velocity, and a position of the user.

19. The method of claim 13, wherein the comparing the activity pattern comprises calculating a range of expected vector values based on recent vector history and the identified activity, and verifying whether one or more measured values fall within the range of expected vector values.

20. The method of claim 13, wherein the angular motion comprises one or more of: an angular acceleration, an angular velocity, an orientation, and an angular momentum of the user.

21. The system of claim 1, further comprising preparing a characterization of the emergency for use by a first responder using the first set of sensor data acquired by the plurality of sensors, wherein the characterization of the emergency comprises one or more of: the activity of the user, a position of the user, an orientation of the user, a motion of the user, a biometric of the user, the first set of sensor data, and a combination thereof.

22. The system of claim 1, wherein the library further comprises a statistical distribution of the plurality of parameter values for the plurality of activity patterns.

* * * * *